United States Patent
Levy

(10) Patent No.: US 8,829,028 B2
(45) Date of Patent: *Sep. 9, 2014

(54) 5-HT4 RECEPTOR ANTAGONISTS FOR THE TREATMENT OF HEART FAILURE

(75) Inventor: Finn Olav Levy, Oslo (NO)

(73) Assignee: Serodus AS, Oslo (NO)

( * ) Notice: Subject to any disclaimer, the term of this patent is extended or adjusted under 35 U.S.C. 154(b) by 540 days.

This patent is subject to a terminal disclaimer.

(21) Appl. No.: 12/372,592

(22) Filed: Feb. 17, 2009

(65) Prior Publication Data

US 2009/0169545 A1 Jul. 2, 2009

Related U.S. Application Data

(63) Continuation of application No. 10/514,386, filed as application No. PCT/GB03/02134 on May 16, 2003, now abandoned.

(30) Foreign Application Priority Data

May 16, 2002 (GB) .................................. 0211230.8

(51) Int. Cl.
| | | |
|---|---|---|
| *A61K 31/436* | (2006.01) | |
| *A61K 31/445* | (2006.01) | |
| *A61K 31/453* | (2006.01) | |
| *A61K 39/395* | (2006.01) | |
| *C07D 405/02* | (2006.01) | |
| *A61K 31/5365* | (2006.01) | |
| *A61K 31/454* | (2006.01) | |
| *C07D 405/12* | (2006.01) | |

(52) U.S. Cl.
CPC .......... *A61K 31/5365* (2013.01); *C07D 405/02* (2013.01); *A61K 31/445* (2013.01); *A61K 31/454* (2013.01); *A61K 2300/00* (2013.01); *C07D 405/12* (2013.01)
USPC ........... 514/321; 514/183; 514/188; 514/205; 514/277

(58) Field of Classification Search
None
See application file for complete search history.

(56) References Cited

U.S. PATENT DOCUMENTS

| | | |
|---|---|---|
| 4,859,683 A | 8/1989 | Youssefyeh et al. |
| 5,137,893 A | 8/1992 | Becker et al. |
| 5,196,547 A | 3/1993 | Becker et al. |
| 5,219,850 A | 6/1993 | Becker et al. |
| 5,260,303 A | 11/1993 | Becker et al. |
| 5,434,161 A | 7/1995 | Becker et al. |
| 5,591,749 A | 1/1997 | Becker et al. |
| 5,604,239 A | 2/1997 | Becker et al. |
| 5,726,187 A | 3/1998 | Gaster et al. |
| 5,852,014 A | 12/1998 | Gaster et al. |
| 5,872,134 A | 2/1999 | King et al. |
| 5,929,089 A | 7/1999 | Jegham et al. |
| 5,990,159 A | 11/1999 | Meulemans et al. |
| 5,998,409 A | 12/1999 | Gaster et al. |
| 6,002,009 A | 12/1999 | Cereda et al. |
| 6,100,339 A | 8/2000 | Watanabe et al. |
| 6,127,379 A | 10/2000 | King et al. |
| 6,255,319 B1 | 7/2001 | Jegham et al. |
| 6,331,401 B1 | 12/2001 | Gerald et al. |
| 6,331,631 B1 | 12/2001 | Fedouloff et al. |
| 6,583,294 B2 | 6/2003 | Fedouloff et al. |
| 6,624,162 B2 | 9/2003 | Uchida et al. |
| 6,946,565 B2 | 9/2005 | Fedouloff et al. |
| 6,979,690 B2 | 12/2005 | Gymer et al. |
| 7,012,080 B2 | 3/2006 | Iguchi et al. |
| 7,834,010 B2 | 11/2010 | Klaveness et al. |
| 2002/0019386 A1 | 2/2002 | King et al. |
| 2002/0128172 A1 | 9/2002 | Sanger et al. |
| 2003/0032640 A1 | 2/2003 | Buxton et al. |
| 2003/0045452 A1 | 3/2003 | Sanger et al. |
| 2003/0092699 A1 | 5/2003 | Uchida et al. |
| 2004/0034226 A1 | 2/2004 | Uchida et al. |
| 2004/0122043 A1 | 6/2004 | Iguchi et al. |
| 2004/0192911 A1 | 9/2004 | Fedouloff et al. |
| 2005/0075335 A1 | 4/2005 | Buxton et al. |
| 2005/0149580 A1 | 7/2005 | Hattori et al. |
| 2006/0057218 A1 | 3/2006 | Buxton et al. |

FOREIGN PATENT DOCUMENTS

| | | |
|---|---|---|
| AU | 707325 | 7/1999 |
| AU | 742666 | 1/2002 |
| EP | 0 018 002 A1 | 10/1980 |
| EP | 0 201 165 A2 | 11/1986 |
| EP | 0 234 872 A1 | 9/1987 |
| EP | 0 274 867 A2 | 7/1988 |
| EP | 0 307 172 A2 | 3/1989 |
| EP | 0309043 A2 | 3/1989 |
| EP | 0 322 973 A2 | 7/1989 |
| EP | 0 387 431 A1 | 9/1990 |
| EP | 0 501 322 A1 | 9/1992 |

(Continued)

OTHER PUBLICATIONS

Skrabal, M. Z. et al. Pharmacother. (2000). 20(7); pp. 787-804.*

(Continued)

*Primary Examiner* — Kevin S Orwig

(74) *Attorney, Agent, or Firm* — Knobbe, Martens, Olson & Bear, LLP

(57) ABSTRACT

This invention provides the use of a 5-HT$_4$ receptor antagonist in the manufacture of a medicament for treating or preventing heart failure. Particular heart disorders to be treated are selected from the group comprising chronic heart failure, congestive heart failure, chronic congestive heart failure and heart failure resulting from ischaemic heart disease. Methods of treating heart failure using 5-HT$_4$ receptor antagonists and pharmaceutical compositions containing 5-HT$_4$ receptor antagonists are also provided.

25 Claims, 9 Drawing Sheets

(56) References Cited

FOREIGN PATENT DOCUMENTS

| | | |
|---|---|---|
| EP | 0 504 679 A1 | 9/1992 |
| EP | 0884319 A2 | 12/1998 |
| EP | 1 325 921 A2 | 7/2003 |
| ES | 2103675 A1 | 9/1997 |
| JP | 01-258674 | 10/1989 |
| JP | 09-067347 | 3/1997 |
| JP | 10-203987 | 8/1998 |
| JP | 2001-006877 | 1/2001 |
| WO | WO 91/00858 A1 | 1/1991 |
| WO | WO 91/16045 A2 | 10/1991 |
| WO | WO 92/15593 A1 | 9/1992 |
| WO | WO 93/02677 A1 | 2/1993 |
| WO | WO 93/03725 A1 | 3/1993 |
| WO | WO 93/05038 A1 | 3/1993 |
| WO | WO 93/05040 A1 | 3/1993 |
| WO | WO 93/18036 A1 | 3/1993 |
| WO | WO 93/08185 A1 | 4/1993 |
| WO | WO 94/05654 A1 | 3/1994 |
| WO | WO 94/07859 A1 | 4/1994 |
| WO | WO 94/08965 A1 | 4/1994 |
| WO | WO 94/08994 A1 | 4/1994 |
| WO | WO 94/08995 A1 | 4/1994 |
| WO | WO 94/08998 A1 | 4/1994 |
| WO | WO 94/10174 A1 | 5/1994 |
| WO | WO 94/17071 A1 | 8/1994 |
| WO | WO 95/18104 A1 | 7/1995 |
| WO | WO 95/26953 A1 | 10/1995 |
| WO | WO 95/32965 A1 | 12/1995 |
| WO | WO 96/05166 A1 | 2/1996 |
| WO | WO 96/31475 A1 | 10/1996 |
| WO | WO 97/17345 A1 | 5/1997 |
| WO | WO 97/27852 A1 | 8/1997 |
| WO | WO 97/38665 A2 | 10/1997 |
| WO | WO 98/07728 A1 | 2/1998 |
| WO | WO 98/08493 A1 | 3/1998 |
| WO | WO 98/11067 A1 | 3/1998 |
| WO | WO 98/47898 A1 | 10/1998 |
| WO | WO 01/16045 A1 | 8/1999 |
| WO | WO 99/50247 A1 | 10/1999 |
| WO | WO 99/64055 A1 | 12/1999 |
| WO | WO 00/03983 A1 | 1/2000 |
| WO | WO 00/03984 A1 | 1/2000 |
| WO | WO 01/05763 A2 | 1/2001 |
| WO | WO 02/11733 A1 | 2/2002 |
| WO | WO 02/11766 A2 | 2/2002 |
| WO | WO 03/035649 A1 | 5/2003 |
| WO | WO 03/068193 A1 | 8/2003 |
| WO | WO 2004/026869 A1 | 4/2004 |
| WO | WO 2004/104577 A2 | 12/2004 |
| WO | WO 2005/021539 A1 | 3/2005 |
| WO | WO 2005/061483 A2 | 7/2005 |
| WO | WO 2005/068461 A1 | 7/2005 |
| WO | WO 2007/007072 A1 | 1/2007 |
| WO | WO 2007/010390 A1 | 1/2007 |
| WO | WO 2007/149929 A1 | 12/2007 |
| WO | WO 2008/049806 A1 | 5/2008 |

OTHER PUBLICATIONS

Singh, B. N. Medscape web article; Pub. Mar. 30, 2001.*
Grogan, M. et al. Am. J. Cardiol. (1992), 69; pp. 1570-1573.*
U.S. Appl. No. 10/818,301, filed Apr. 5, 2004, Fedouloff et al.
U.S. Appl. No. 10/055,817, filed Jan. 23, 2002, Buxton et al.
U.S. Appl. No. 11/054,387, filed Feb. 10, 2005, Hattori et al.
U.S. Appl. No. 11/203,573, filed Aug. 9, 2005, Buxton et al.
(2000) "Information Update vol. 1-24 No. 12" in 1 page, with Piboserod Hydrochloride SB-207266A "Treatment of IBS 5-HT4 antagonist", *Drugs of the Future*, 25:1323.
*Annual Drug Data Report* (1993) SB-207710 and SB-205800, 10:949.
Bach, T. et al. (2001) "5-HT$_4$(a) and 5_HT4(b) receptors have nearly identical pharmacology and are both expressed in human atrium and ventricle" *Naunyn-Schmiedeberg's Arch. Pharmacol.* 363:146-160.
Baxter, G.S. et al. (1991) "t-hydroxytryptamine4 receptors mediate relaxation of the rat oesophageal tunica muscularis mucosae" *Naunyn-Schmiedeberg's Archives of Pharmacology* 343:439-446.
Bharucha, A.E. et al. (2000) "Effects of a serotonin 5-HT4 receptor antagonist SB-207266 on gastrointestinal motor and sensory function in humans" *Gut* 47:667-674.
Blondel, O. et al. (1997) "Molecular and functional characterization of a 5-HT$_4$ receptor cloned from human atrium" *FEBS Letters* 412:465-474.
Blondel, O. et al. (1998) "Cloning, expression, and pharmacology of four human 5-hydroxytryptamine4 receptor isoforms produced by alternative splicing in the carboxyl terminus" *J. Neurochem.* 70:2252-2261.
Blondel, O. et al. (1998) "The 5-HT$_4$ receptor antagonist ML10375 inhibits the constitutive activity of human 5-HT$_4$(c) receptor" *Brit. J. Pharmacol.* 125:595-597.
Bockaert, J. et al. (1992) "The 5-HT4 receptor: a place in the sun" *TiPS* 13:141-145.
Bockaert, J. et al. (1994) "5-HT4 receptors potential therapeutic implications in neurology and psychiatry" *CNS Drugs* 1:6-15.
Bonhaus, D. et al. (1994) "[3H]RS-23597-190, a potent 5-hydroxytryptamine4 antagonist labels SIGMA-1 but not SIGMA-2 binding sites in guinea pig brain" *J. Pharmacol. Exp. Ther.* 271:484-493.
Brattelid, T. et al. (2004) "Functional serotonin 5-HT4 receptors in porcine and human ventricular myocardium with increased 5-HT4 mRNA in heart failure" *Naunyn-Schmiedeberg's Arch. Pharmacol.* 370:157-166.
Braunwald, E. et al. (2000) "Congestive heart failure: fifty years of progress" *Circulation* 102:IV-14-IV-23.
Bristow, M. (2000) "βadrenergic receptor blockade in chronic heart failure" *Circulation* 101:558-569.
Clark, R. (1998) "Medicinal chemistry of 5-HT4 receptor ligands" Ch. 1, *5-HT$_4$ Receptors in the Brain and Periphery*, pp. 1-48, Richard M. Eglen (Ed.), Springer-Verlag, Germany.
Clark, R. et al. (1995) "RS-100235: a high affinity 5-HT4 receptor antagonist" *Bioorg. Med. Chem. Lett.* 5:2199-2122.
Cohen, M. et al. (1996) "LY353433, a potent, orally effective, long-acting 5-HT$_4$ receptor antagonist: comparison to cisapride and RS23597-190" *J. Pharmacol. Exp. Ther.* 277:97-104.
Dumuis, A. et al. (1988) "A 5-HT receptor in the central nervous system, positively coupled with adenylate cyclase, is antagonized by ICS 205 930" *Eur. J. Pharmacol.* 146:187-188.
Eglen, R. et al. (1995) "Central 5-HT4 receptors" *TiPS* 16:391-397.
Ford, A.P.D.W. et al. (1993) "The 5-HT4 receptor" *Med. Res. Rev.* 13:633-662.
Gale, J. et al. (1994) "GR125487: A selective and high affinity 5-HT$_4$ receptor antagonist" *Brit. J. Pharmacol.* 113:120P.
Gaster, L. et al. (1993) "Communications to the Editor: (1-Butyl-4-piperidinyl)methyl 8-amino-7chloro1,4-genzodioxane-5-carboxylate hydrochloride: a highly potent and selective 5-HT4 receptor antagonist derived from metoclopramide" *J. Med. Chem.* 36:4121-4123.
Gaster, L. et al. (1995) "Communications to the Editor: N-[(1-butyl-4-piperidinyl)methyl]-3,4-dihydro-2h-[1,3]oxazino[3,2-a]indole10-carboxamide hydrochloride: the first potent and selective 5-HT$_4$ receptor antagonist amide with oral activity" *J. Med. Chem.* 38:4760-4763.
Gaster, L. (1997) "5-HT4 receptor antagonist agent for irritable bowel syndrome" *Drugs of the Future* 22: 1325-1332.
Gerald, C. et al. (1995) "The 5-HT$_4$ receptor: molecular cloning and pharmacological characterization of two splice variants" *The EMBO Journal* 14:2806-2815.
Gullikson, G.W. et al. (1992) "Gastrointestinal motility responses to the S and R enantiomers of zacopride, a 5-HT4 agonist and 5-HT3 antagonist" *Drug Dev. Res.* 26:405-417.
Hagihara, K. et al. (1994) "Antagonistic activities of N-3389, a newly synthesized diazabicyclo derivative, at 5-HT$_3$ and 5-HT$_4$ receptors" *Eur. J. Pharmacol.* 271:159-166.
Jahnel, U. et al. (1992) "Positive inotropic response to 5-HT in human atrial but not in ventricular heart muscle" *Naunyn-Schmiedeberg's Arch. Pharmacol.* 346:482-485.

(56) References Cited

OTHER PUBLICATIONS

Joubert, L. et al. (2002) "A 5-HT$_4$ receptor transmembrane network implicated in the activity of inverse agonists but not agonists" *J.BioL Chem.* 277:25502-25511.

Kadowaki, M. et al. (1993) "Effect of FK1052, a potent 5 hydroxytryptamine$_3$ and 5-hydroxytryptamine4 receptor dual antagonist, on colonic function in vivo" *J. Pharmacol. Exp. Ther.* 266:74-80.

Kajita, S. et al. (2001) "Pharmacological characterization of a novel 5-HT$_4$ receptor agonist, TS-951, in vitro" *Pharmacology* 63:8-16.

Kaumann, A. et al. (1991) "A 5-HT4-like receptor in human right atrium" *Naunyn-Schmiedeberg's Arch. Pharmacol.* 344:150-159.

Kaumann, A. (1993) "Blockade of human atrial 5-HT$_4$ receptors by GR 113808" *Br. J. Pharmacol.* 110:1172-1174.

Kaumann, A. (1994) "Blockade of human atrial 5-HT$_4$ receptors by SB 207710, a selective and high affinity 5-HT$_4$ receptor antagonist" *Naunyn-Schmiedeberg's Arch. Pharmacol.* 349:546-548.

Kaumann, A. (1994) "Do human atrial 5-HT$_4$ receptors mediate arrhythmias?" *TiPS* 15:451-455.

Kaumann, A. et al. (1994) "5-hycroxytryptamine causes rate-dependent arrhythmias through 5-ht4 receptors in human atrium: facilitation by chronic β-adrenoceptor blockade" *Naunyn-Schmiedeberg's Arch. Pharmacol.* 349:331-337.

Laer, S. et al. (1998) "Receptor mechanisms involved in the 5-HT-induced inotropic action in the rat isolated atrium" *Brit. J.Pharmacol.* 123:1182-1188.

Lefebvre, H. et al. (1998) "Effect of the serotonin4 receptor agonist cisapride on plasma aldosterone levels in cirrhotic patients with secondary hyperaldosteronism" *Eur. J. Clin. Pharmacol.* 53:479-480.

Lemaire, S. et al. (1998) "Heart rate as a determinant of L-type Ca2+ channel activity: mechanisms and implication of force-frequency relation" *Basic Research iCardiol.* 93 (Suppl. 1):51-59.

Leung, E. et al. (1996) "Comparison of 5-HT$_4$ receptors in guinea-pig colon and rat oesophagus: effects of novel agonists and antagonists" *Naunyn-Schmiedeberg's Arch. Pharmacol.* 354:145-156.

Lorrain, J. (1992) "5-HT4 receptors, present in piglet atria and sensitive to SDZ 205-557, are absent in papillary muscle" *Eur. J. Pharmacol.* 229:105-108.

McLean, P. et al. (1995) "5-HT$_4$ receptor antagonist affinities of SB207710, SB205008, and SB203186 in the human colon, rat oesophagus, and guinea-pig ileium peristaltic reflex" *Naunyn-Schmiedeberg's Arch. Pharmacol.* 352:132-140.

Meulemans, A. (1992) "Is the action of cisapride on the guinea-pig ileium mediated via 5-HT$_4$ receptors?" *Eur. J.Pharmacol.* 212:51-59.

*The Merck Manual of Diagnosis and Therapy*, (1999) 17$^{th}$ Edition, Chapter 203 "Heart Failure", Mark H. Beers, M.D. and Robert Berkow, M.D., Editors, pp. 1682-1704.

Mine, Y. et al. (1997) "Comparison of effect of mosapride citrate and existing 5-HT4 receptor agonists on gastrointestinal motility in vovo and in vitro" *JPET* 283:1000-1008.

Parker, S. et al. (1995) "Blockade of human and porcine myocardial 5-HT4 receptors by SD 203186" *Naunyn-Schmiedeberg's Arch. Pharmacol.* 353:28-35.

Pitt, B. (1999) "The effect of spironolactone on morbidity and mortality in patients with severe heart failure" *The New England Journal of Medicine* 341:709-717.

Qvigstad, E. et al. (2005) "Appearance of a ventricular 5-HT4 receptor-mediated inotropic response to serotonin in heart failure" *Cardiovascular Research* 65:869-878.

Rahme, M. et al. (1999) "Electrophysiological and antiarrhythmic effects of the atrial selective 5-HT$_4$ receptor antagonist RS-100302 in experimental atrial flutter and fibrillation" *Circulation* 100:2010-2017.

Reeves, J.J. et al. (1991) "Investigation into the 5-hydroxytryptamine receptor mediating smooth muscle relaxation in the rat oesophagus" *Br. J. Pharmacol.* 103:1067-1072.

Romanelli, M.N. et al. (1993) "Synthesis and biological activity of a series of aryl tropanyl esters and amides chemically related to 1h-indole-3-carboxylic acid endo 8-methyl-8-azabicyclo[3.2.1] oct-3-yl ester" *Arzheim Forsch./Drug Res.*, 43:913-918.

Sanders, L. et al. (1992) "A 5-HT4-like receptor in human left atrium" *Naunyn-Schmiedeberg's Archives of Pharmacology* 345:382-386.

Saxena, P. et al. (1992) "5-Hydroxytryptamine-induced increase in left ventricular dP/dt$_{max}$ does not suggest the presence of ventricular 5-HT$_4$ receptors in the pig" *Naunyn-Schmiedeberg's Arch. Pharmacol.* 346:629-636.

Schoemaker, R. et al. (1992) "5-Hydroxytryptamine increases contractile force in porcine right atrium but not in left ventricle" *Naunyn-Schmiedeberg's Arch. Pharmacol.* 346:486-489.

Schoemaker, R. et al. (1993) "5-Hydroxytryptamine stimulates human isolated atrium but not ventricle" *Eur. J. Pharmacol.* 230:103-105.

Scifinder Scholar Search, Sep. 19, 2006, in respect of compound SB207226.

Scifinder Scholar Search, Sep. 19, 2006, in respect of compound SC56184.

Steele, P. (1994) Meeting Highlights "5$^{th}$ Symposium on medicinal chemistry in Eastern England" *Exp. Opin. Invest. Drugs* 3:767-769.

Torres, G. et al. (1994) "Antagonists of 5-HT$_4$ receptor-mediated responses in adult hippocampal neurons" *J.. Pharmacol. Exp. Ther.* 71:255-261.

Watanabe, K. et al. (2000) "Effects of cisapride and protective effects of mexiletine on the qt interval in rats" *Acta Medica et Biologica* 48:113-117.

Weber, K.T. (1999) "Aldosterone and spironolactone in Heart Failure" *The New England Journal of Medicine* 341:752-755.

Weber, K.T. (2001) "Aldosterone in congestive heart failure" *The New England Journal of Medicine* 345:1689-1697.

Webster'S Dictionary, 1963, Merriam-Webster, p. 1798.

Yang, D. et al. (1993) "SC-53606, a potent and selective antagonist of 5-hydroxytryptamine$_4$ receptors in isolated rat esophageal tunica muscularis mucosae" *J. Pharmacol. Exp. Ther.* 266:1339-1347.

Zerkowski, H-R. et al. (1993) "Comparison of the positive inotropic effects of serotonin, histamine, angiotensinlI, endothelin and isoprenaline in the isolated human right atrium" *Naunyn-Schmiedeberg's Archives of Pharmacology* 347:347-352.

Zhou, H. et al. (2001) "The effects of tegaserod (HTF 919) on the pharmacokinetics and pharmacodynamics of digoxin in healthy subjects" *J. Clin. Pharmacol.* 41:1131-1139.

Birkeland, J.A.K. et al. 2007 "Effects of treatment with a 5-HT$_4$ receptor antagonist in heart failure" *Br J Pharmacol* 150: 143-152.

Hunt, S.A. et al. 2001 "ACC/AHA Guidelines for the Evaluation and Management of Chronic Heart Failure in the Adult: Executive Summary a Report of the American College of Cardiology/American Heart Association Task Force on Practice Guidelines (Committee to Revise the 1995 Guidelines for the Evaluation and Management of Heart Failure)" *Circulation* 104: 2996-3007.

Fuster, V. et al. 2001 "ACC/AHA/ESC guidelines for the management of patients with atrial fibrillation; A report of the American College of Cardiology/American Heart Association Task Force on Practice Guidelines and the European Society of Cardiology Committee for Practice Guidelines and Policy Conferences (Committee to develop guidelines for the management of patients with atrial fibrillation) developed in collaboration with the North American Society of Pacing and Electrophysiology" *European Heart Journal* 22: 1852-1923.

Qvigstad, E. et al. 2005 "Appearance of ventricular 5-HT$_4$ receptor-mediated ionotropic response to serotonin in heart failure" *Cardiovascular Research* 65: 869-878.

Jamieson, C. et al. 2006 "Medicinal Chemistry of hERG Optimizations: Highlights and Hang-Ups" *Journal of Medicinal Chemistry* 49: 5029-5046.

\* cited by examiner

SEQUENCE LISTING

```
<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: synthetic primer

<400> SEQUENCE: 1
catgtgcata ggtatacagt ggaatgt

<210> SEQ ID NO 2
<211> LENGTH: 21
<212> TYPE: DNA
<213> ORGANISM: Artificial Sequence
<220> FEATURE:
<223> OTHER INFORMATION: synthetic primer

<400> SEQUENCE: 2
```

-continued gcagccacca aaggagaagt t                                    21

<210> SEQ ID NO 3
<211> LENGTH: 30
<212> TYPE: DNA
<213> ORGANISM: Artificial Sequence
<220> FEATURE:
<223> OTHER INFORMATION: synthetic probe

<400> SEQUENCE: 3
ccatctgctg ccagcctttg gtctatagga                           30

<210> SEQ ID NO 4
<211> LENGTH: 19
<212> TYPE: DNA
<213> ORGANISM: Artificial Sequence
<220> FEATURE:
<223> OTHER INFORMATION: synthetic primer

<400> SEQUENCE: 4
ttcaccacag ccgcttcaa                                       19

<210> SEQ ID NO 5
<211> LENGTH: 25
<212> TYPE: DNA
<213> ORGANISM: Artificial Sequence
<220> FEATURE:
<223> OTHER INFORMATION: synthetic primer

<400> SEQUENCE: 5
atcctgtagt ccaaagactg ggatt                                25

<210> SEQ ID NO 6
<211> LENGTH: 38
<212> TYPE: DNA
<213> ORGANISM: Artificial Sequence
<220> FEATURE:
<223> OTHER INFORMATION: synthetic probe

<400> SEQUENCE: 6
atggatatac ctacagatat ggtcgtccac acggcaat                  38

<210> SEQ ID NO 7
<211> LENGTH: 21
<212> TYPE: DNA
<213> ORGANISM: Artificial Sequence
<220> FEATURE:
<223> OTHER INFORMATION: synthetic primer

<400> SEQUENCE: 7
atctgatgga tttcaagaac c                                    21

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
ctctgagacg ggttgacttc                                      20

<210> SEQ ID NO 9
<211> LENGTH: 23
<212> TYPE: DNA

```
<213> ORGANISM: Artificial Sequence
<220> FEATURE:
<223> OTHER INFORMATION: synthetic probe

<400> SEQUENCE: 9
cgcttcatcg gtctgctcgc tca                                        23

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
cctgcaccac caactgctta                                            20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
ggcatggact gtggtcatga                                            20

<210> SEQ ID NO 12
<211> LENGTH: 27
<212> TYPE: DNA
<213> ORGANISM: Artificial Sequence
<220> FEATURE:
<223> OTHER INFORMATION: synthetic probe

<400> SEQUENCE: 12
tggccaaggt catccatgac aactttg                                    27
```

5-HT4 RECEPTOR ANTAGONISTS FOR THE TREATMENT OF HEART FAILURE

RELATED APPLICATIONS

This Application is a Continuation of U.S. patent application Ser. No. 10/514,386 filed Aug. 26, 2005 which is the U.S. National Phase under 35 U.S.C. §371 of International Application PCT/GB03/02134, filed May 16, 2003 designating the U.S., and published in English as WO 03/097065 on Nov. 27, 2003, which claims priority to Great Britain Patent Application No. 0211230.8 filed May 16, 2002, all of which are incorporated herein by reference in their entireties.

FIELD OF THE INVENTION

The present invention relates to heart failure and in particular the use of 5-HT$_4$ receptor antagonists for the treatment of heart failure and the symptoms associated therewith.

DESCRIPTION OF THE RELATED ART

Heart failure is a disease that primarily affects the elderly and with a population which is ageing progressively it is likely that the prevalence of this disease will continue to increase. New and improved methods of treating heart failure are therefore required.

Heart disorders or diseases, which are generally characterised by impaired cardiac function, e.g., heart failure, affect a large number of people worldwide and in particular in the Western world. Heart disorders or diseases are responsible for a reduced quality of life and premature death in a significant proportion of sufferers. Heart disorders occur in men, women, and children of both sexes, but are particularly prevalent in men and in elderly or middle aged people.

Heart failure is characterized by impaired cardiac function either due to reduced pump function (systolic dysfunction) or reduced filling (diastolic dysfunction). There are a number of different causes of heart failure of which the most common in the western world is coronary artery disease. Other common causes are cardiomyopathy (primary or secondary), hypertension, valvular diseases, and congenital defects.

Approximately 70% of heart failure in the western world is caused by coronary artery disease, which is usually due to atherosclerosis. Atherosclerosis will result in narrowing of the vessels in the heart leading to inadequate blood supply to the myocardium (muscle cells). Such heart disorders which involve a reduced supply of blood to the heart are sometimes given the general term "ischemic heart disease". Ischemic heart disease (or ischemic cardiomyopathy) is the major etiologic group of heart failure in the Western world.

A reduced blood supply to the heart can manifest itself as angina pectoris (pain in the chest), acute myocardial infarction (which is the result of acute coronary artery occlusion causing a damaged myocardium with scar tissue; such an area cannot sustain cardiac muscle function), and sudden deaths. If the blood supply to the heart is reduced over periods of weeks to years, or if the myocardium has been substantially weakened by infarction with scar tissue, the heart function will become weakened with reduced pumping ability leading to the clinical manifestation of chronic heart failure.

Congestive heart failure (CHF, of which chronic congestive heart failure (cCHF) is a subset), is characterised by impaired left ventricular function, increased peripheral and pulmonary vascular resistance and reduced exercise tolerance and dyspnea. Circulatory congestion results from the decrease in cardiac output or from the damming of blood in the veins behind the left or right heart.

The more common forms of heart failure that result from damage to the heart often cannot be cured, but treatment may improve symptoms.

Current treatment for heart failure is based partially on preventative measures such as controlling diet, for example reducing or excluding caffeine and sodium, weight loss and exercise. Surgical means are used in more serious cases, for example coronary bypass surgery which eases symptoms by increasing bloodflow to the heart, coronary angioplasty or transplantation, if the heart has lost significant pumping capacity.

Drug treatments are also used. For example angiotensin converting enzyme (ACE) inhibitors slow the progression of heart failure by inhibiting the formation of angiotensin and causing vasodilation. The use of other diuretics is also common, which relieve water retention in the body thus easing the workload on the heart. Digitalis preparations such as digoxin are also used to increase the force of the heart's contractions.

Betablockers are another commonly used treatment for heart failure, alone or in combination with ACE inhibitors. The failing heart is adrenergically activated, in contrast to the normally functioning human ventricle when in a resting state (Bristow, 2000, Circulation, Vol 101, 558-569). The increase in cardiac adrenergic drive appears to be damaging to the failing heart and is thus termed a maladaptive response. This response appears to be associated with changes in the composition of the adrenoceptors during heart failure with up-regulation of $\alpha_1$ adrenoceptors and the down-regulation of $\beta$ adrenoceptors. In addition, mouse models overexpressing activated adrenoceptors show cardiomyopathy and systolic dysfunction. Chronic adrenergic signalling is therefore considered to be a harmful compensatory mechanism in the failing human heart.

In the end stage failing heart, 50-60% of the total signal transducing potential is lost. lockade of the remaining signalling capacity using betablockers complements the heart's endogenous antiadrenergic strategy of desensitisation, which is considered to be an adaptive change (Bristow, 2000, Circulation, Vol 101, 558-569).

By inhibiting the remaining signalling potential of $\beta$ adrenergic receptors using $\beta$ blockers, a relatively effective method of treating heart failure has been developed and used with some success.

Nonetheless, whilst $\beta$ blockers have been used with relative success, there is a continuing need for further drugs and treatments for heart disease. $\beta$ blocker treatment is not successful for all patients as some patients show contraindications to $\beta$ blockade such as reactive airways disease, sinus node or conduction system disease with bradycardia. Furthermore the target doses require careful manipulation and management for the desired result to be achieved. Another disadvantage is that some individuals do not respond to $\beta$-blockade (Bristow, 2000, Circulation, Vol 101, 558-569). The disadvantages of known treatments and increasing incidence of heart disease as the age of the population increases means that more treatments are required.

SUMMARY OF THE INVENTION

The present invention addresses this need and is based on the surprising discovery that 5-HT$_4$ receptors mediate an inotropic response in rat papillary heart muscles from failing hearts, a response which is not observed in normal rat papillary heart muscles. Thus, an inotropic response to serotonin (5-HT) appears to be induced in the ventricles of failing hearts. This surprising observation suggests that this inotropic response may be a further maladaptive compensatory mechanism in the failing heart. Based on this, a new therapy is proposed, namely to reduce or prevent this inotropic response to 5-HT (5-hydroxytryptamine; serotonin) by blocking the 5-HT$_4$ receptors e.g., by the use of 5-HT$_4$ receptor antagonists. Thus, we propose that a potential new treatment for heart failure lies in the use of 5-HT$_4$ receptor antagonists.

5-HT is known to affect the CNS, the heart and the gastrointestinal tract. Effects on the heart include positive inotropic, chronotropic and lusitropic effects, all of which have been detected to date only on human atrial tissue and not ventricular tissue. In the human atrium these effects are mediated via the 5-HT$_4$ receptors. Activation of the 5-HT$_4$ receptor, which is a 7 transmembrane G-protein coupled receptor causes the stimulation of adenylyl cyclase activity, activation of cAMP dependent protein kinase and the phosphorylation of proteins involved in excitation-contraction coupling.

The 5-HT$_4$ class of receptors is one of 7 known classes of 5-HT receptors (5-HT$_{1-7}$). All but one of the identified receptors are 7 transmembrane-spanning G-protein coupled receptors. Several of these classes contain more than one member, encoded either by separate genes or by splice variants. The 5-HT$_4$ receptor has at least eight splice variants (5-HT$_{4(a)}$-5-HT$_{4(h)}$). Preliminary studies have suggested that differential expression of these splice variants may occur in different tissues although it has also been shown that certain splice variants may be coexpressed in some tissues. The precise role of the different splice variants is not yet clear.

Previous studies have identified 5-HT responses in human and porcine atrial tissue, occurring via the 5-HT$_4$ receptor, including increased heart rate, contractile force and hastening of relaxation. These studies failed to show any effect of 5-HT on human (Jahnel et al., 1992, Naunyn Schmiedeberg's Arch Pharmacol, Vol 346:482-485; Schoemaker et al European Journal of Pharmacology 1993 Vol 230, 103-105) and porcine (Schoemaker et al., 1992, Naunyn Schmiedeberg's Arch. Pharmacol, 346: 486-489; Lorrain et al. 1992, Eur J Pharmacol 229: 105-108; Saxena, 1992, Naunyn Schmiedeberg's Arch. Pharmacol, 346: 629-636) ventricles. In addition, 5-HT$_4$ receptors were thought to be localised exclusively in the atrium (Blondel et al., 1998, Journal of Neurochemistry Vol 70(6), 2252-2261, Blondel et al., 1997, FEBS Letters Vol. 412, 465-474).

A recent publication by Bach et al (2001, Naunyn Schmiedeberg's Arch. Pharmacol, 363; 146-160) however shows that the mRNA encoding 5-HT$_4$ receptors is detectable in all 4 chambers of the normal human heart by RT-PCR. Co-expression of the 5-HT$_{4(a)}$ and 5-HT$_{4(b)}$ variants in both cardiac atrium and ventricle was shown. However, no functional studies of the receptors were reported.

5-HT$_4$ receptor antagonists (such as that disclosed by WO 93/02677) have been proposed for use in the treatment of atrial arrhythmias and stroke, in addition to irritable bowel syndrome, gastro-oesophageal reflux disease, anxiety and/or migraine (WO 91/16045, Kaumann 1994 TiPS Vol 15, 451-455).

No previous studies have suggested any involvement or effect of the 5-HT$_4$ receptor on heart failure, or any effects of heart failure on this receptor.

As mentioned above, it has now surprisingly been shown that the potential inotropic response (the force of muscular contraction) to 5-HT differs in papillary muscles from non-failing and failing rat heart, and in particular that only papillary muscles from failing rat hearts show a response to 5-HT (see Example 1).

We have further surprisingly shown that this inotropic effect is mediated through 5-HT$_4$ receptors. The observation that 5-HT$_4$ receptors are functional in failing rat heart muscle, and not in normal rat heart muscle indicates that this induction and signalling may be a novel compensatory mechanism in heart failure. By the term "compensatory mechanism" it is meant that the heart adapts to its reduced ability to function, in an attempt to compensate for decreased pumping. The adaptation, as in this case, and in the case of the β-adrenergic system, may take the form of an adaptation, or induced changes in signalling mechanisms and pathways. Thus, blocking this compensatory mechanism, for example, by using an antagonist of 5-HT$_4$ receptors, presents a novel and hitherto unforeseen treatment modality in combatting heart failure.

The fact that human papillary muscles taken from patients with different types of heart failure also exhibit an inotropic response to serotonin, that is mediated by 5-HT$_4$ receptors (Example 6) confirms that this effect is not restricted to rats.

It has also been shown that 5-HT$_{4(b)}$ mRNA levels are increased in left ventricle and in papillary muscle in rats with CHF.

Thus, in one aspect, the present invention provides the use of 5-HT$_4$ receptor antagonists in the manufacture of a medicament for combatting heart failure.

Also provided is a method of combatting heart failure in a mammal, said method comprising administering a 5-HT$_4$ receptor antagonist to said mammal. Particularly, an effective amount of said antagonist is administered.

In still a further aspect, the invention also provides a 5-HT$_4$ receptor antagonist, or a pharmaceutical composition containing such an antagonist for use in combatting heart failure.

Still further, is provided the use of a 5-HT$_4$ receptor antagonist for combatting heart failure.

DETAILED DESCRIPTION OF THE PREFERRED EMBODIMENT

Figure 1:
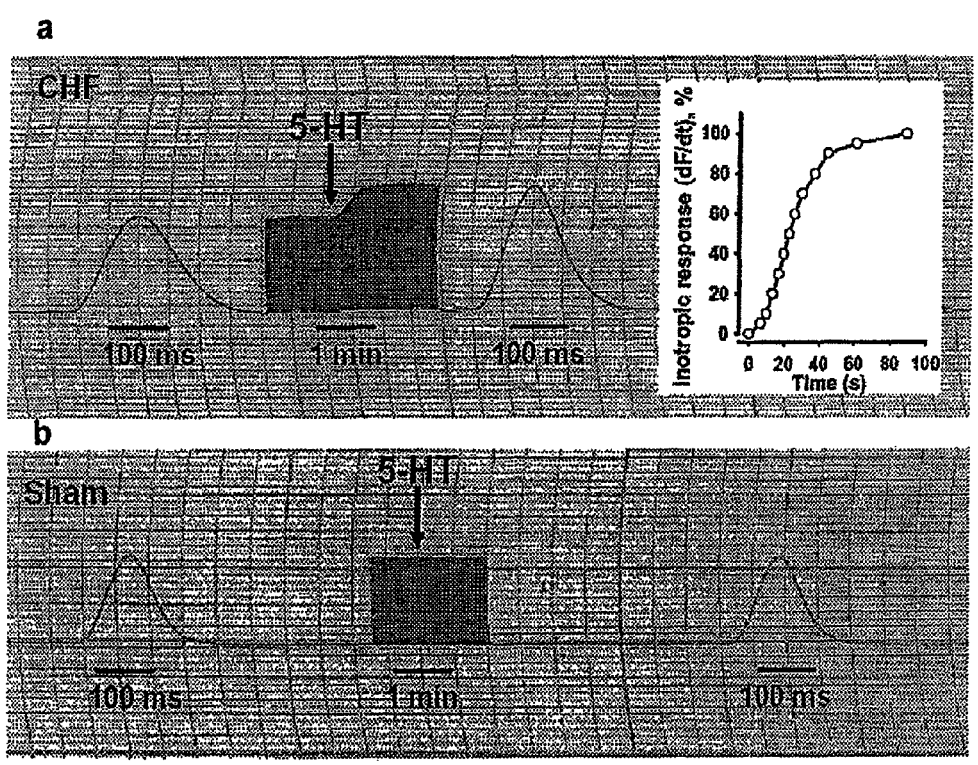
FIG. 1 shows the inotropic effect of serotonin in heart failure rats. Original paper recording in a papillary muscle from a representative Chronic heart failure rat. Serotonin (10 μmol/l) induced a positive inotropic response in the presence of atropine, timolol and prazosin. Inset: Development of the inotropic response, expressed as F$_{max}$ in percent of individual maximal response, in Chronic heart failure papillary muscles following addition of serotonin to 10 μmol/l. Horizontal error bar represents time±SEM to 50% relative response. The time needed to reach each percentile is the mean value from 10 papillary muscles.

The mechanism by which the inotropic response to 5-HT is induced in heart failure has not yet been elucidated, but in any event, it is not critical to the proposed new therapeutic approach. However, whilst not wishing to be bound by theory, the mechanism of induction of the inotropic response may result from a functional activation of pre-existing inactive receptors whether through a structural or topological change, or release of inhibition. Alternatively the pre-existing receptors may be transported to a location where they can act. The mechanism may alternatively be increased synthesis, or induction, of novel receptors through increased transcription or translation. It is therefore to be understood that "induction" may refer to any mechanism whereby the activity of the 5-HT$_4$ receptor signalling pathway is increased when compared to the activity in a normal (e.g. non-failing) heart.

In particular, the "induction" includes any mechanism whereby the 5-HT$_4$ receptor mediated inotropic response is induced or increased. An "increase" is preferably or conveniently a statistically significant increase, for example in a test for 5-HT$_4$ receptor mediated response as described in Example 1, or in any other test for inotropic response known in the art or described in the literature.

The term "heart failure" as used herein includes any condition characterised by impaired cardiac function either due to reduced pump action (systolic dysfunction) or reduced filling (diastolic dysfunction). More particularly, heart failure implies impaired function of the myocardium of the heart. Particularly, chronic forms of heart failure (i.e. chronic heart failure) in general are concerned. Alternatively viewed, a subset of heart failure of particular interest is congestive heart failure (CHF), and especially chronic congestive heart failure (cCHF). However other forms of heart failure are encompassed by the invention. The invention does not however include other heart diseases or conditions which do not come under the general definition of heart failure, as above, such as atrial arrythmias which are excluded from the scope of this invention.

Thus, heart failure can be defined as a disorder which may result from any condition that reduces the ability of the heart to pump blood. Often the cause is decreased contractility of the myocardium resulting from diminished coronary blood flow (e.g., heart failure caused by coronary artery disease (CAD) or coronary ischemic disease), but failure to pump adequate quantities of blood can also be caused by damage to heart valves, external pressure around the heart, primary cardiac muscle diseases (e.g., idiopathic dilated cardiomyopathy) or any other abnormality which makes the heart a hypo-effective pump. As mentioned above, chronic heart failure is particularly concerned.

Thus included in the scope of the invention are ischaemic heart disease (ischaemic cardiomyopathy), particularly chronic ischaemic heart disease, chronic non-ischaemic cardiomyopathy including idiopathic dilated cardiomyopathy and cardiomyopathy due to hypertension.

Cardiac failure may be manifest in either of two ways: (1) by a decrease in cardiac output or (2) by a damming of blood in the veins behind the left or right heart. The heart can fail as a whole unit or either the left side or the right side can fail independently of the other. Either way this type of heart failure leads to circulatory congestion and, as a result is referred to as congestive heart failure (CHF).

Congestive heart failure can be divided into two phases, acute (short term and unstable) CHF and chronic (long term and relatively stable) CHF. The division between the two is difficult to define precisely, but generally acute CHF is the stage of failure which occurs immediately after heart damage (i.e. has a rapid onset and short course) and is associated with instability in cardiac function and circulation, for example a sudden drop in cardiac output. Providing the acute phase is not so severe as to result in death, the sympathetic reflexes of the body are immediately activated and can compensate for the sudden loss in cardiac function. Such compensation can often be so effective and rapid that it is possible that no noticeable effect on the patient will be felt if a patient remains calm.

After the first few minutes of an acute heart attack, a prolonged secondary state begins. This is characterized by a retention of fluid by the kidneys and by the progressive recovery of the heart over a period of several weeks to months up until the point at which the cardiac condition stabilises. This phase of stability is known as chronic CHF. Although the heart has compensated and stabilised it is still weak and may become progressively weaker.

This means therefore that although symptoms vary largely between patients, patients with chronic CHF characteristically have a reduced cardiac function. The most common manifestation of reduced cardiac performance is systolic dysfunction. For example such patients display a reduced left ventricular ejection fraction (LVEF) when compared to a "normal" person who has not suffered from heart failure. In normal persons left ventricular ejection fraction is usually above 60%, while an ejection fraction less than 40% is characterized as systolic dysfunction. Thus, a LVEF of less than 40% is characteristic of reduced heart function in patients with chronic CHF. Less common than systolic dysfunction is diastolic dysfunction in which the ejection fraction is relatively preserved (left ventricular EF>40%) or normal, but where left ventricular filling is reduced.

Other characteristics of reduced cardiac function such as for example a reduced right ventricular ejection fraction, reduced exercise capacity and impaired haemodynamic variables such as a decreased cardiac output, increased pulmonary arterial pressure and increased heart rate and low blood pressure are also often observed in patients with cCHF.

The New York Heart Association (NYHA) classification system divides heart disease into four classes, depending on the severity of disease. NYHA class I: Patient with cardiac disease but without resulting limitations of physical activity; Class II: Patient with cardiac disease resulting in slight limitation of physical activity. Class III: Patient with cardiac disease resulting in marked limitation of physical performance. They are comfortable at rest. Class IV: Patient with cardiac disease resulting in inability to carry on any physical activity without discomfort. Symptoms may be present at rest.

The invention may be used for the treatment of all classes of heart failure but particularly the classes II-IV.

As alluded to above, heart failure in general may be chronic or acute. Thus, while the acute phase of heart failure (for example CHF) is over relatively quickly, the stability associated with the chronic phase of heart failure (e.g., CHF) can take a matter of months to develop. Generally, a patient exhibiting symptoms of heart failure for greater than 3 months or more preferably greater than 6 months can be regarded as having chronic stable heart failure, providing that no further symptoms of acute (e.g., congestive) heart failure such as angina or evidence of myocardial infarction have occurred during this 3 month or 6 month period.

As was alluded to briefly above, the chronic heart failure to be treated according to the present invention may result from any cause, e.g., may be the result of a primary disease or may be secondary to another disease. In one preferred embodiment of the invention the chronic heart failure to be treated is secondary to either idiopathic dilated cardiomyopathy (IDCM) and/or coronary ischemic disease (coronary artery disease—CAD).

Particularly, in a further preferred embodiment, the heart failure to be treated according to the invention is post-infarction heart failure. It will be noted in this regard that the rat model used in Example 1, 2, 4 and 7 is a model of post-infarction heart failure caused by coronary artery ligation, which is a well characterised model of heart failure.

Other types of heart failure which may be treated according to the invention include heart failure induced by a constantly increased after load, such as hypertensive heart failure. A rat model for this is also available, wherein heart failure is induced by aortic banding. This model has also been used to show that the 5-$HT_4$ receptor mediated effect is not specific to post infarction heart failure (see Example 5).

The term "combatting" as used herein includes both treatment and prevention.

The term "5-$HT_4$ receptor antagonist" as used herein includes any agent, i.e., any compound, substance, molecule or composition (or any other agent) which may reduce or prevent any response, for example an inotropic response, to 5-HT in heart failure (i.e., the response (e.g., inotropic response) of the heart, or preferably of the myocardium). Thus the antagonist may be viewed as any agent capable of inhibiting the inotropic response to 5-HT, or any other physiological or biological response to 5-HT. This activity may readily be assessed using any appropriate response test, for example any inotropic response test, available in the art, for example as detailed in Example 1. Thus, an inhibition may be observed as a decrease (e.g., a statistically significant decrease) in the response in question (e.g., inotropic response) in the presence of the agent as compared with the response (e.g., inotropic response) in the absence of the agent (i.e., antagonist).

Any agent known in the art and/or reported in the literature as an antagonist of 5-5-$HT_4$ receptors may be used (including inverse agonists and partial agonists etc. which may function as antagonists under particular conditions, e.g. dosages/concentrations etc.).

Thus, the term "5-$HT_4$ receptor antagonist" as used herein includes any compound, molecule, substance, agent or composition which attenuates the effect of 5-HT on the 5-$HT_4$ receptor. Such antagonism may be competitive or non-competitive. Competitive antagonists bind to the receptor at a region that overlaps with the agonist binding site, thereby preventing the binding of the agonist. The negative log of the molar concentration which at equilibrium would occupy 50% of receptors in the absence of ligand ($pK_B$) is the measure of potency of a competitive antagonist. Non-competitive antagonists bind to a site on the receptors other than the site of agonist binding and prevent agonist binding and/or receptor activation via an allosteric mechanism. In addition, antagonists may be reversible or irreversible. Antagonists may readily be identified by their activity at the 5-$HT_4$ receptor using any suitable assay or test system, conveniently any in vitro system using cells expressing stably or transiently transfected recombinant 5-$HT_4$ receptors or endogenous 5-$HT_4$ receptors, such as those described by Bach et al., (2001, supra).

Classically, receptor antagonists are small organic compounds and these represent a preferred class of 5-$HT_4$ receptor antagonists for use according to the present invention. However, other "compounds" or "agents" may also be used; so long as they meet the functional criterion of inhibiting an inotropic (or any other) response to 5-HT (e.g., by blocking or inhibiting a 5-HT$_4$ receptor) their chemical or physical nature is unimportant. hus, for example protein or peptide molecules may be used, which may be natural or synthetic, or derivatives or modifications of natural molecules. One such class of protein/peptide molecules is antibodies and their fragments or derivatives, including synthetic antibody-like molecules. Many such "binding molecules" based on antibodies are known in the art e.g., single chain antibodies, CDR grafted antibodies, chimeric antibodies etc., and all such molecules are included. Alternatively, peptides and other molecular products of display or other (e.g., combinatorial) libraries may be used; the literature describes the synthesis and selection of many such binding molecules or binding entities by such display or other methods, and these may be used, selected to bind to the 5-HT$_4$ receptor.

Also included are the salts of such compounds, including both organic and inorganic salts (e.g., with alkali and alkaline earth metals, ammonium, ethanolamine, diethanolamine and meglumine, chloride, hydrogen carbonate, phosphate, sulphate and acetate counterions). Appropriate pharmaceutically and/or physiologically acceptable salts are well described in the pharmaceutical literature. In addition, some of these salts may form solvates with water or organic solvents such as ethanol. Such solvates are also included within the scope of this invention.

5-HT$_4$ receptor antagonists may also be prepared as prodrugs according to principles well known in the art (e.g., as compounds which release, or which convert to, the active antagonist form when administered to the patient).

5-HT$_4$ receptor antagonists are known in the art and described in the literature (Clark, R. D. in 5-HT$_4$ Receptors in the Brain and Periphery, ed R. Eglen 1998 Springer Verlag and R. G. Landes Company). Any such compounds may be used according to the present invention. Thus, for example 5-HT$_4$ receptor antagonists may be selected from compounds comprising an aromatic ring structure with a hydrogen-bond acceptor as one substituent and a hydrogen-bond acceptor as a second substituent and a tertiary amine spaced with at least three bonds away from the aromatic ring.

The 5-HT$_4$ receptor antagonists are preferably selected from compounds comprising an aromatic ring to which a carbonyl group is attached, and a basic nitrogen in the appended side chain. An oxygen atom is preferably adjacent to the carbonyl group.

Representative classes of suitable compounds include benzoate esters, benzoate amides, imidazolopyridines, aryl ketones, indoles, carbazimidamides, phenylcarbamates and phenylureas.

Further examples of 5-HT$_4$ receptor antagonists that could be used in the invention include: SB203186, 1-piperidinylethyl-1H-indole-3-carboxylate (Parker S G et. al. Naunyn Schmiedebergs Arch Pharmacol. 1995 December; 353(1): 28-35); GR113808, [1-[2-methylsulphonylamino ethyl]-4-piperidinyl]methyl1-methyl-1H-indole-3-carboxylate (Kaumann A J. Br J. Pharmacol. 1993 November; 110(3): 1172-4); SB207710, (1-butyl-4-piperidinyl)methyl 8-amino-7-iodo-1,4-benzodioxan-5-carboxylate (Kaumann A J et. al. Naunyn Schmiedebergs Arch Pharmacol. 1994 May; 349(5): 546-8); SDZ205557, 2-diethylaminoethyl-(2-methoxy-4-amino-5-chloro)benzoate (Lorrain J et. al. Eur J. Pharmacol. 1992 Dec. 8; 229(1): 105-8); DAU 6285, endo-8-methyl-8-azabicyclo [3.2.1]oct-3-yl-2,3-dihydro-6-methoxy-2-oxo-1H-benzimidazole-1-carboxylate (Torres G E et. al. J Pharmacol Exp Ther. 1994 October; 271(1): 255-61); RS 39604, 1-[4-amino-5-chloro-2-(3,5-dimethoxybenzyloxy)phenyl]-3 [1-[2-[(methylsulf-onyl)amino]ethyl]-4-piperidinyl]-1-propanone hydrochloride (Leung E et. al. Naunyn Schmiedebergs Arch Pharmacol. 1996 July; 354(2): 145-56); SB 204070, (1-n-butyl-4-piperidinyl)methyl 8-amino-7-chloro-1,4-benzodioxane-5-carboxylate (Leung E. et al. supra); SB 207266, N-[(1-butyl-4-piperidinyl)methyl]-3,4-dihydro-2H-[1,3]oxazino[3,2-a]indole-locarboxamide hydrochloride (Gaster L M et. al. J. Med. Chem. 1995 Nov. 24; 38(24): 4760-3); SB205008, 1-butyl-1-methyl-4-piperidinylmethyl)-8-amino-7-chloro-1,4-benzodioxan-5-carboxylate iodide (McLean P G and Coupar I M. Naunyn Schmiedebergs Arch Pharmacol. 1995 August; 352(2): 132-40); (1-Butyl-4-piperidinyl)methyl 8-amino-7-chloro-1,4-benzodioxane-5-carboxylate hydrochloride (Gaster L M et al. J Med. Chem. 1993 Dec. 10; 36(25): 4121-3); N-3389, (endo-3,9-dimethyl-3,9-diazabicyclo[3,3,1]non-7-yl 1H-indazole-3-carboxamide dihydrochloride) (Hagihara K et. al. Eur J. Pharmacol. 1994 Dec. 12; 271(1): 159-66); FK1052, [(+)-8,9-dihydro-10-methyl-7-[(5-methyl-4-imidazolyl)methyl]pyrido-[1,2-a-]-indole-6(7H)-one hydrochloride] (Kadowaki M et. al. J Pharmacol Exp Ther 1993 July; 266(1): 74-80); ML10375, 2-(cis-3,5-dimethylpiperidino)ethyl 4-amino-5-chloro-2-methoxybenzoate (Blondel O et. al. Br J. Pharmacol. 1998 October; 125(4): 595-7); RS-23597-190, [3-(piperidine-1-yl) propyl-4-amino-5-chloro-2-methoxybenzoate hydrochloride] (Bonhaus D W et. al. J Pharmacol Exp Ther. 1994 October; 271(1): 484-93); GR125487, (1-[2-[(methyl-sulphonyl)amino]ethyl]-4-piperidinyl-methyl-5-fluoro-2-methoxy-1H-indole-3-carboxylate) (Gale et al 1994 Br. J. Pharmacol., 113, 120P); (3-α-tropanyl)-1H-indazole-3-carboxylic acid (WO91/16045); ICS205-930 (tropisetron) (Dumuis A. et al. (1998), Eur J. Pharmacology 146 187-188); R50595 (FR76530) (Meulemans A L and Schuurkes J A. (1992), Eur J. Pharmacol. 212(1):51-9); RS 100235 (Clark R. D. et al. (1995) Bioorg Med Chem Lett; 5; 2119-2122); RS100302 (Rahme et al., 1999, Circulation 100(9): 1942-4); LY353433, 1-(1-methylethyl)-N-[2-[4-[tricyclo[3.3.1.1(3,7)]dec.sup.-1-ylcarbonyl)amino]-1-piperidinyl]ethyl-1H-indazole-3-carb-oxamide, (Cohen M. L. et al. J Pharmacol Exp Ther 1996; 277(1): 97-104); RO116-0086, 2,3-dihydrobenzo [1,4]dioxine-5-carboxylic acid 1-butyl-piperidin-4-ylmethyl ester hydrochloride salt, (Joubert L. et al., J Biol. Chem. 2002, 277: 2250); RO116-1148 (2,3-dihydrobenzo[1,4]-dioxine-5-carboxylic acid 1-butyl-piperidin-4-ylmethyl amide hydrochloride salt) Joubert et al. 2002, supra) A-85380 (WO94/ 08994); SB205800 (Drug Data Report (1993) 15 10:949); SB 207058 (Exp Opin Invest Drugs (1994) 3(7):767); SB 207226 (Marketletter 22-1 en 22-18 (1995)); SC-53606 (Yang D C et al (1993) J Pharmacol Exp Ther; 266(3):1339-47); SC 56184 (R&D Focus (1993) 2(37)10).

However other 5-HT$_4$ receptor antagonists may also be used.

5-HT$_4$ receptor antagonists are further described in the following patent documents: WO91/16045, WO93/02677, WO93/18036, WO93/05040, WO 93/03725, WO 93/05038, PCT/EP93/03054, PCT/GB93/01895, PCT/EP93/02808, PCT/GB93/02028, PCT/EP93/02775, PCT/EP93/02809, PCT/GB93/02130, PCT/GB94/00172 (all to Smith Kline Beecham plc), EP-A-501322 (Glaxo), U.S. Pat. No. 6,331, 401 (Synaptic Pharmaceutical Corporation), US 20020128172 (GlaxoSmithKline), US 20030045452 (GlaxoSmithKline), US 20020019386 (GlaxoSmithKline), EP-A-322973 (GlaxoSmithKline), EP-A-18002 (Sandoz Limited), U.S. Pat. No. 5,872,134 (Smith Kline Beecham), EP-A-387431 (Beecham Group plc), EP-A-201165 (Beecham Group plc), EP-A-201165 (Beecham Group plc), EP-A-234872 (Adria), U.S. Pat. No. 4,859,683 (Rorer), EP-A-307172 (Lilly), U.S. Pat. No. 6,127,379 (Smith Kline Beecham), U.S. Pat. No. 6,002,009 (Boehringer Ingelheim), U.S. Pat. No. 5,929,089 (Synthelabo) and U.S. Pat. No. 5,726,187 (Smith Kline Beecham).

By definition, as explained above, the 5-HT$_4$ receptor antagonists will inhibit any 5-5-HT$_4$ receptor mediated action of 5-HT in the failing heart. The antagonist may thus for example inhibit all 5-HT$_4$ receptor mediated actions. By inhibition is meant that the response to 5-HT, for example the inotropic response, when compared to an untreated individual, is reduced. This reduction includes any measurable decrease in a response to 5-HT (e.g., the ventricular inotropic response) in an individual when compared to the 5-HT response (e.g., the ventricular inotropic response) in an individual taken at an earlier time, before treatment. The measurable decrease will preferably be statistically significant. More preferably the measurable decrease will be such that the 5-HT response (e.g., the ventricular inotropic response) is substantially inhibited by the 5-HT$_4$ receptor antagonist. Most preferably the response is blocked. By blocked it is meant that no measurable response (e.g., the inotropic response) to 5-HT is detected in the presence of the 5-HT receptor antagonist.

Especially preferably the decrease will be associated with the improved cardiac performance of the patient.

Cardiac performance may be assessed according to methods and practices well known in the art.

Given the nature of most forms of heart disease it is not to be expected that "treatment" in accordance with the present invention will result in a complete cure of the heart failure in question. Rather, "treatment" in accordance with the present invention includes an improvement or alleviation of any of the symptoms associated with the heart failure and also an improved quality of life for a patient and, ultimately a prolonged lifetime and improved survival. "Treatment" in accordance with the present invention also includes an improvement or increase of the functionality of the heart or, in other words an improvement or increase in cardiac function or performance. In particular, treatment in accordance with the present invention may result in an improvement or increase in any one or more of the symptoms and functional parameters associated with heart failure patients and in particular the following symptoms and parameters of the patient.

The first symptom and parameter associated with improved cardiac function in heart failure patients is an increase in ventricular ejection fraction and in particular left ventricular ejection fraction (LVEF). This can be assessed by standard methods well known and documented in the art, for example by echocardiography, ECG synchronized gated radionuclide ventriculography (MUGA scan), angiography or magnetic resonance (MR) imaging, and is normally carried out when the subject is at rest. An improvement in LVEF has been found to be associated with improved survival amongst CHF patients (Cintron et al., 1993, Circulation Vol 87, Supplement VI, 17-23). Thus, this is an important and advantageous parameter to be improved in subjects treated in accordance with the present invention. RVEF may also be increased.

Whilst an improvement of LVEF is particularly important for the overall improvement of heart function, a number of other parameters associated with cardiac performance may be improved in accordance with the present invention. One of these is a significant improvement in overall clinical status and thus clinical performance as evaluated by NYHA functional class. In other words the NYHA functional class of a patient may be reduced after treatment with 5-HT$_4$ antagonists in accordance with the present invention. Such a clinical evaluation may normally be carried out by a trained cardiologist.

Also an improvement may be seen in exercise capacity of the patients, as measured by peak oxygen uptake and peak work load. As indicated above, a decreased exercise capacity is an inconvenient and potentially dehabilitating symptom of many heart failure patients. Methods for measuring exercise capacity are well known and documented in the art. For example exercise testing can be carried out using an electrically braked bicycle ergometer. An exemplary protocol might consist of a starting work rate of 20 W increasing by 20 W every second minute until exhaustion (defined as an inability to keep the pedalling rate steady at 60 rpm). Oxygen uptake (VO$_2$) can be measured using for example the EOS/SPRINT system. Peak VO$_2$, is taken as the highest VO$_2$ observed.

Furthermore various improvements in hemodynamic status and echocardiographic variables may also be observed. These are again indicative of improved cardiac function. For example a significant decrease in pulmonary capillary wedged pressure and in pulmonary artery pressure may be observed, together with an increase in peak heart rate, peak systolic blood pressure and mitral velocity deceleration time. Echocardiographic variables may conveniently be measured by echocardiography carried out by a trained cardiologist and haemodynamic variables can conveniently be assessed by right-sided heart catheterization according to standard techniques.

Another important variable which may be assessed is the plasma level of Nt-proANP. An increased or generally high level of Nt-proANP has been recognised as a marker of cardiac dysfunction. Moreover, levels of Nt-proANP have been shown in the past to correlate with pulmonary artery pressures in CHF and provide important prognostic information in CHF patients (Gottlieb et al., J. Am. Coll. Cardiol. 1989; 13: 1534-1539). Levels of Nt-proANP in a blood sample can be measured in a number of ways well known and documented in the art, for example by radioimmunoassay. Prior to the immunoassay, plasma is separated from a blood sample taken from the patient again by methods well known and documented in the art.

The above described "improvement" or "increase" in the symptoms and parameters includes any measurable improvement or increase when the parameter in question is compared with the equivalent parameter in a non-treated individual or when the parameter in question is compared with the equivalent parameter in the same individual taken at an earlier time point (e.g., comparison with a "base line" level). Preferably the improvement or increase will be a statistically significant one. Especially preferably the improvement or increase in the symptoms and parameters will be associated with the improved health of the patient concerned and more preferably a prolonged survival.

Methods of determining the statistical significance of differences in parameters are well known and documented in the art. For example herein a parameter is generally regarded as significant if a statistical comparison using a two-tailed significance test such as a Student t-test or Mann-Whitney U Rank-Sum test shows a probability value of <0.05.

Thus, a further aspect of the present invention relates to the use of a 5-HT$_4$ receptor antagonist in the manufacture of a medicament for use in the improvement of cardiac function, particularly cardiac function in heart failure.

In a yet further and more preferred aspect, the present invention relates to the use of a 5-HT$_4$ receptor antagonist in the manufacture of a medicament for use in the increase of ventricular function, particularly preferably left ventricular function (e.g., LVEF), more particularly in heart failure.

A yet further aspect of the present invention relates to the use of a 5-HT$_4$ receptor antagonist in the manufacture of a medicament for use in the reduction of plasma Nt-proANP levels. As mentioned above, a reduction in the plasma levels of Nt-proANP is an indicator of improved cardiac function and performance. "Reduction" as used herein includes any measurable reduction when the parameter in question is compared with the equivalent parameter in a non-treated individual or when the parameter in question is compared with the equivalent parameter in the same individual taken at an earlier time point (e.g., comparison with a "base line" level). Preferably the reduction is statistically significant as discussed above. Especially preferably the reduction in the levels of Nt-proANP will be associated with an improved feeling of health in the patient concerned and more preferably a prolonged survival.

Alternatively viewed, the invention provides a method of improving cardiac function in a mammal (for example a mammal with heart failure) which method comprises administering to said mammal a pharmaceutically effective amount of a 5-$HT_4$ receptor antagonist.

The above described uses and methods are generally carried out on mammals. Any mammal may be treated, for example humans and any livestock or domestic animal, e.g., mice, rats, pigs, cats, dogs, sheep, rabbits, horses, cows or monkeys. However, preferably the mammals are humans.

The 5-$HT_4$ receptor antagonist is conveniently formulated in a pharmaceutical composition for use according to the present invention. Thus, as mentioned above in a further aspect, the present invention also provides a pharmaceutical composition for use in combatting heart failure, said composition comprising a 5-$HT_4$ receptor antagonist together with at least one pharmaceutically acceptable carrier diluent or excipient.

The appropriate content of active ingredient in such compositions may be determined according to principles and procedures routine in the art and may readily be determined by the skilled practitioner. Thus, for example, the active ingredient in such compositions may comprise from 0.05% to 99% by weight of the formulation, for example from 0.1% to 1.0% or around 0.5%. The concentration of active ingredient in the formulation will depend on the type of formulation. For example, enteral products (e.g., tablets and capsules) can typically have 5% to 50% active ingredients by weight, whereas parenteral formulations usually have a lower concentration of active compound e.g. 0.1% to 3% active ingredient by weight, for example in an injection solution.

By "pharmaceutically acceptable" is meant that the ingredients must be compatible with other ingredients of the composition as well as physiologically acceptable to the recipient.

The pharmaceutical compositions may be formulated according to any of the conventional methods known in the art and widely described in the literature. Thus, the active ingredient (i.e., 5-$HT_4$ receptor antagonist) may be incorporated, optionally together with other active substances, with one or more conventional carriers, diluents and/or excipients, to produce conventional galenic preparations which are suitable or can be made suitable for subcutaneous, intramuscular, intravenous or any other administration such as powders, sachets, cachets, elixirs, suspensions, emulsions, solutions, syrups, ointments, sterile injectable solutions, sterile packaged powders, and the like. The pharmaceutical composition comprising the 5-$HT_4$ receptor antagonist may be prepared in a form appropriate for infusion or injection into a patient. Such infusion or injection is preferably intravenous (i.v.) but may also be given subcutaneously (s.c.) or intramuscularly (i.m.).

Preferably, the compositions may be provided in a form adapted for oral or parenteral administration. Alternative pharmaceutical forms thus include plain or coated tablets, capsules, suspensions and solutions containing the active component optionally together with one or more inert conventional carriers and/or diluents.

Examples of suitable carriers, excipients, and diluents are lactose, dextrose, sucrose, maltose, glucose, sorbitol, mannitol, starches, gum acacia, calcium phosphate, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavouring agents, and the like. The compositions of the invention may be formulated so as to provide quick, sustained or delayed release of the active ingredient after administration to the patient by employing procedures well known in the art.

Solubilizing and/or stabilizing agents may also be used, e.g., cyclodextrins (CD) α, β, γ and HP-β cyclodextrin.

Suitable doses will vary from patient to patient and can be determined by the physician in accordance with the weight, age and sex of the patient, mode of administration, and the severity of the condition and also the particular antagonist used for treatment. Exemplary unit doses for oral administration contain 1 to 250 mg (and for parenteral administration contains preferably from 0.1 to 50 mg), of the active ingredient. The daily dose for oral administration is normally in the range of approximately 0.01 to 10 mg/kg/day, more usually 0.1 to 5 mg/kg/day, for example 0.1 to 2 mg/kg/day. For example a 70 kg adult would receive a daily dose of 1 to 700 mg or 0.7 to 700 mg, more usually 1 to 350 mg or 7 to 350 mg for example 7 to 140 mg. For intravenous or intramuscular administration the doses can be between 0.1 mg and 100 mg, preferably between 0.1 mg and 25 mg, the compound being administered 1 to 4 times a day.

The improvements seen in patients treated in accordance with the present invention may be immediate (e.g., after a few days), or may be seen after a few weeks or a few months depending on the individual patient. Once the initial improvement is seen, continued improvement over the subsequent weeks and months may also occur. As indicated above, treatment can be continued for as long as is desired or is necessary.

Use of a 5-$HT_4$ receptor antagonist in accordance with the present invention may be in place of, or preferably in addition to (i.e., in combination with) the use of other drugs for treatment of heart failure. Thus, other drugs known to treat heart failure might be included in the pharmaceutical compositions described above or may be administered separately, in a manner appropriate for the drug concerned.

Thus, in a further aspect the present invention provides a product comprising (a) a 5-$HT_4$ receptor antagonist and (b) a second drug (e.g., a second agent effective for the treatment of heart failure) as a combined preparation for simultaneous, separate or sequential use in the treatment of heart failure or in improving cardiac function.

Suitable 5-$HT_4$ receptor antagonists are defined above. Suitable second drugs or agents are well known and documented in the art and include known drugs for use in the treatment of heart disorders, for example diuretics, vasodilators, inotropic drugs such as digoxin, or other compounds such as anticoagulants, β blockers, angiotensin II blockers, angiotensin converting enzyme inhibitors or aldosterone antagonists may be used as discussed above.

A particularly advantageous combination of 5-$HT_4$ receptor antagonist is with β-blockers.

The invention will be further described with reference to the following non-limiting Examples with reference to the following drawings in which:

EXAMPLE 1

Animals

Animals were cared for according to the Norwegian Animal Welfare Act which conforms with the Guide for the Care and Use of Laboratory Animals published by the US National Institutes of Health (NIH publication No 85-23, revised 1996). Two rats were kept in each cage and housed in a temperature regulated room with a 12-h day/12-h night cycling and allowed free access to water and food.
Heart Failure Model Induction of Myocardial Infarction Male, Wistar rats (Mollegaard Breeding and Research Centre, Skensved, Denmark), weighing about 320 g were intubated and ventilated with 68% $N_2O$, 29% $O_2$ and 2-3% Isofluran (Abbot Laboratories, USA). An extensive myocardial infarction (MI) was induced by a proximal ligation of the left coronary artery. Six weeks later the rats were anaesthetized and ventilated on the respirator with 2.2% Isofluran. Left ventricular pressures were measured (Sjaastad et al., 2000, J. Appl. Physiol, 89: 1445-1454), and Chronic heart failure rats were included in the study if left ventricular end diastolic pressure (LVEDP) was >15 mm Hg. Typically, the infarct comprised most of the left ventricular free wall and also extended to the apex and the base of the papillary muscle. Echocardiography has previously demonstrated severely depressed myocardial function (Sjaastad et al. 200, supra). The sham-operated animals (SHAM) were subjected to the same surgical procedure but the coronary artery was not ligated.
Isolated Papillary Muscles Hearts were isolated from the anaesthetized animals (see above) and carefully dissected free of connective tissue and transferred to ice cold 0.9% NaCl and weighed. The aorta was cannulated, and the coronaries were perfused at 31° C. with a relaxing solution containing: (mmol/l) NaCl 118.3; KCl 3.0; $CaCl_2$ 0.5; $MgSO_4$ 4.0; $KH_2PO_4$ 2.4; $NaHCO_3$ 24.9; glucose 10.0; mannitol 2.2 and equilibrated with 95% $O_2$/5% $CO_2$ at 31° C. (pH 7.4). Posterior left ventricular papillary muscle was ligated The muscles were transported to a separate laboratory and mounted in organ baths. In order to prevent contracture of the papillary muscles during transportation and mounting, we used a relaxing solution with a $Ca^{++}/Mg^{++}$ concentration ratio of 1:8 comparable to that of St. Thomas' Hospital cardioplegic solution. The papillary muscles were mounted in organ baths containing the relaxing solution and allowed to adapt at 31° C. for about 20 minutes before the solution was changed to one containing the following (in mmol/l): NaCJ 119.2; KCJ 3.0; $CaCl_2$ 2.0; $MgSO_4$ 1.2; $KH_2PO_4$ 2.4; $NaHCO_3$ 24.9; glucose 10.0; mannitol 2.22 and equilibrated with 95% $O_2$/5% $CO_2$ at 31° C. (pH 7.4).

The muscles were field stimulated with alternating polarity at 1 Hz with impulses of 5 msec duration and current about 20% above individual threshold (10-15 mA, determined in each experiment). The isometrically contracting muscles were stretched to the maximum of their length-tension curve. The force was recorded and analysed as previously described (Skomedal et al., 1997, J. Pharmacol. Exp. Ther. 280: 721-729). The muscles were allowed to equilibrate for 90 minutes. When used, prazosin ($\alpha_1$-AR antagonist), timolol ($\beta$-AR antagonist), ketanserin ($5-HT_{2A}$ selective antagonist) and GR113808 ($5-HT_4$-selective antagonist) were allowed to act for 90 minutes before addition of agonist. Averaged contraction-relaxation cycles (CRC) were calculated for different experimental periods, and these cycles were used to determine descriptive parameters like maximal development of force $(dF/dt)_{max}$, time to peak force (TPF) and time to relaxation to 20% level (TR2O). Relaxation time (RT) was calculated as TR2O-TPF. $(dF/dt)_{max}$ was used as an index of contractility. Inotropic responses induced by agonists were expressed by increase in $(dF/dt)_{max}$. RT was used as index of relaxation. Lusitropic responses were expressed as reduction in RT. Mechanical response at the end of the equilibrium period was used as the control response.
Experimental Design Agonist was added cumulatively or as a single bolus directly to the organ baths and was completely mixed in the solution within 2-3 seconds. The concentration-dependent inotropic and lusitropic responses to $5-HT_4$-receptor stimulation by serotonin were obtained in the presence of prazosin (1 μmol/l) and timolol (3 μmol/l or 1 μmol/l) atropine (1 μmol/l) and ascorbate (10 μmol/l), respectively. Concentration-response curves for serotonin were obtained by adding serotonin cumulatively in the absence and presence of ketanserin (0.1 μmol/l). Concentration-response curves for $5-HT_4$-receptor stimulation in the presence of ketanserin were performed in the absence and presence of 0.5 nmol/l GR13808 and the relative shift of the curves was used to calculate the $K_b$ for GR113808. When serotonin was added as a single dose (10 μmol/l) the experiments were performed in the absence of ketanserin. The presence of either antagonist did not influence the basal or maximal function of the muscles with regard to mechanical performance or electrical stimulation threshold (data not shown). The different agonists were added directly to the organ baths in increasing concentrations until supramaximal concentrations of agonist were obtained with respect to maximal inotropic response.
Calculation and Statistics The responses for each concentration of agonist were generally calculated as percent of maximal response. The concentration-response curves constructed from papillary muscle experiment were constructed according to Ariens and Simonis (1964, supra), by estimating centiles ($EC_{10}$ to $EC_{100}$) for each single experiment and calculating the corresponding means. This calculation provides mean curves that express the response as fractional response or percent of maximum and display horizontal positioning and the correct mean slope of the curves. The horizontal positioning of the concentration-response curves was expressed as $pEC_{50}$-values (=−log $EC_{50}$). Data are expressed as mean±standard error of the mean (SEM) and the number of animals expressed as n. The significance levels of differences were calculated according to Students t-test. P<0.05 is considered statistically significant. The inhibition constants $K_b$ were calculated from the Schild equation, based on the relative shifts of the concentration-response curves for receptor stimulation.
Drugs Serotonin (5-hydroxytryptamine hydrochloride, 5-HT) was from Sigma (St. Louis, Mo., USA). GR 113808 ({1-[2-(methyl-sulphonylamino)ethyl]-4-piperidinyl}methyl 1-methyl-1H-indole-3-carboxylate) maleate was from Tocris (Bristol, UK). Ketanserin (3-[2-[4-(4-fluorobenzoyl)-1-piperidinyl]ethyl]-2,4(1H,3H)-quinazolinedione) tartrate was from RBI (Natick, Mass., USA). Prazosin hydrochloride, timolol maleate. (−)-isoprenaline hemisulphate, ascorbate, carbamylcholine (carbachol) and atropine sulfate were purchased from Sigma. Stock solutions were prepared in double destilled water and kept at minus 20° C. to avoid oxidation. Further dilutions of the drugs were made fresh daily and kept cool (0-4° C.).

Results

Inotropic Effects of Serotonin in Heart Failure Rats

Figure 2A:
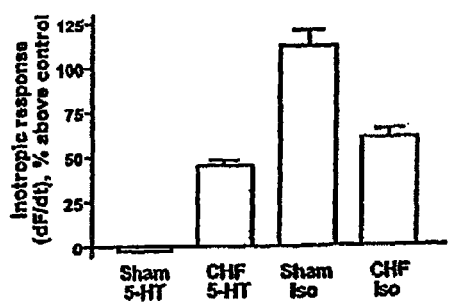
FIG. 2 shows the inotropic response to serotonin (10 μmol/l) and isoprenaline (100 μmol/l) in papillary muscles from Chronic heart failure and sham-operated rats. a) Increase in development of force expressed as percent above control. b) Representative examples of single recordings of contraction-relaxation cycles in a papillary muscle exposed to serotonin and isoprenaline. The figure shows representative contractions before addition of agonist (_), at maximal steady state inotropic response to 10 μmol/l serotonin ( - - - - ) and at maximal steady state inotropic response to 100 μmol/l isoprenaline ( . . . . ). Ordinate: Development of tension in arbitrary units. Abscissa: Time after initiating stimulus.

In the presence of prazosin, atropine and timolol 10 µmol/l of serotonin elicited a monophasic positive inotropic response not seen in sham-operated animals (n=6) (FIG. 1, 2a). With a lag phase (diffusion delay) of about 5 seconds the time from addition of serotonin to 50% relative inotropic response was 22±2.0 sec, and to maximal inotropic response 1-2 minutes (FIG. 1, inset). The serotonin mediated increase in contractile force in papillary muscles from post-MI heart failure rats was 44.5±2.9% (SEM, n=10), comparable to the inotropic effect of 10 µmol/l isoprenaline 60.4±5.8% (or 58.5±7%) (SEM, n=10) (FIG. 2a). The inotropic responses through the respective receptors were not additive indicating coupling to the same signalling pathway. In sham-operated animals, however, isoprenaline evoked a positive inotropic response of 111.6±8.6% (mean±SEM, n=6) (FIG. 2a) underlining the attenuation of the mechanical response to β-adrenoceptor stimulation in failing myocardium.

Qualitative Characteristics of the Inotropic Response to Serotonin

Figure 2B:
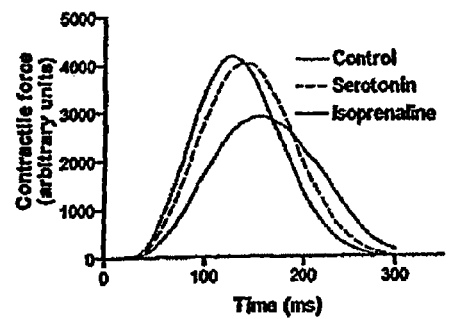

The inotropic response to serotonin induced qualitative changes in the contraction-relaxation cycles (FIG. 2b) not observed in sham-operated animals. Time to peak force in the control period was 148.0±3.9 ms (mean±SEM, n=8) and after stimulation by serotonin there was a shortening of the contraction-relaxation cycles with a significant reduction in TPF, TR2O and RT (table 1). These changes reflect a selective increase in relaxation compared to contraction, which is comparable to what is observed during β-adrenoceptor stimulation in myocardial preparations (Skomedal et al. 1997, supra), and consistent with common signalling pathways for these agents.

Figure 3:
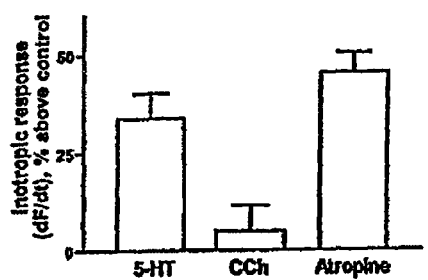
FIG. 3 shows the reversal of the inotropic response to serotonin by cholinergic stimulation. The figure shows the increase in contractile force expressed as percent above control in papillary muscles from Chronic heart failure rats in response to cumulative addition of 10 μmol/l serotonin (5-HT), 30 μmol/l carbachol (CCh) and 1 μmol/l atropine (Atropine). Note that carbachol reversed and atropine restored the inotropic response to serotonin.

Influence of Cholinergic Stimulation on the Inotropic Response Induced by Serotonin Stimulation of muscarinic acetylcholine receptors is well known to exert a functional antagonism of inotropic effects mediated through $G_{\alpha S}$-adenylyl cyclase-pathway and as a pharmacological approach to elucidate the involvement of such a pathway in the serotonin induced inotropic response we stimulated these receptors with carbachol. 10 µmol/l of serotonin exerted a positive inotropic response of 33.7±6.6% (mean±SEM, n=5) above control level. Carbachol (30 µmol/l) reversed the response to 4.8±6.5% (mean±SEM, p<0.01) within 2-3 seconds (or 1-2 minutes) (FIG. 3) and partially reversed TPF, TR2O and RT. Atropine (1 µmol/) restored the response to 45.1±5.1% (mean±SEM, p>0.06 vs. serotonin alone, 2-tailed paired t-test) and re-established the contraction-relaxation cycle characteristics, suggesting an involvement of the $G_{\alpha S}$-adenylyl cyclase-pathway.

Reversal of the Inotropic Response Induced by Serotonin by the 5-HT-Selective Antagonist GR113808

Figure 4:
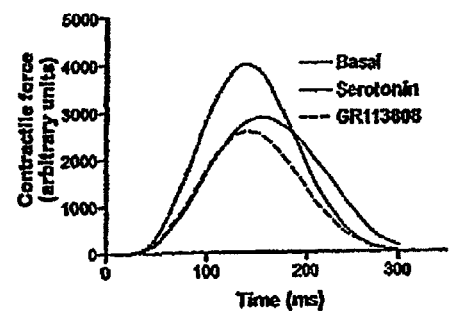
FIG. 4 shows the reversal of the inotropic response to serotonin by the 5-HT$_4$-selective antagonist GR113808. The figure shows representative contraction-relaxation cycles in a papillary muscle from a Chronic heart failure rat before addition of agonist (_), at maximal steady state inotropic response to 10 µmol/l serotonin ( . . . . ) and following reversal by 1 µmol/l GR113808 ( - - - - ). Ordinate: Development of tension in arbitrary units. Abscissa: Time after initiating stimulus.

The qualitative characteristics of the inotropic response to serotonin, its similarity to the inotropic response to isoprenaline and the reversal by carbachol all indicated an involvement of the $G_s$-adenylyl cyclase-pathway. Three different serotonin-receptors couple to G, and stimulation of adenylyl cyclase, 5-HT$_4$, 5-HT$_6$ and 5-HT$_7$ (Hoyer et al., 1994, Pharmacol. Rev. 46: 157-203). Of these, the 5-HT$_4$ receptor is known to mediate inotropic and chronotropic effects in human and porcine atrium (Kaumann, 1994, Trends Pharmacol. Sci. 15: 451-455), albeit not in rat (Laer et al., 1998, Br. J. Pharmacol. 123: 1182-1188). We therefore tested whether a 5-HT$_4$-selective serotonin receptor antagonist would block the serotonin-mediated inotropic response in papillary muscle from Chronic heart failure rats. GR113808 is a selective 5-HT$_4$-antagonist with a pKi of 9.2-9.7 (Gale et al., 1994, Br. J. Pharmacol. 111: 332-338), and 1 µmol/l GR113808 completely reversed the inotropic response evoked by 10 µmol/l serotonin (FIG. 4). The shortening of the contraction-relaxation cycles induced by serotonin was also sensitive to GR113808. However, as seen from FIG. 4, these serotonin-induced changes were not completely reversed when GR113808 was given subsequent to serotonin. This is a typical finding with cAMP-mediated stimulation of inotropy (Skomedal et al., 1997, supra), and does not detract from the fact that GR113808 was able to fully reverse the effects of serotonin.

Lack of Ketanserin Effect Eliminates Involvement of 5-HT$_{2A}$ Receptors

Figure 5:
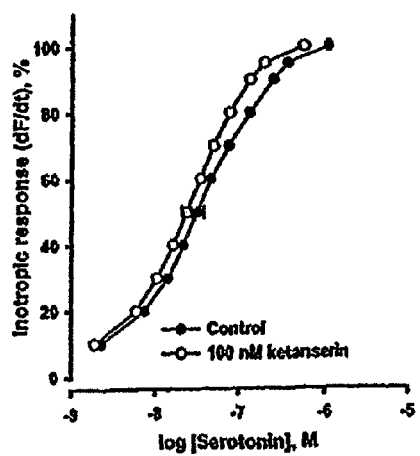
FIG. 5 shows that the lack of ketanserin effect eliminates involvement of 5-HT$_{2A}$-receptors. Concentration-response curves for serotonin in papillary muscles from Chronic heart failure rats in the absence and presence of 0.1 µmol/l ketanserin. Inotropic response was measured as dF/dt and is expressed in percent of maximum in each experiment. The concentration of serotonin needed to reach each percentile was calculated for each experiment according to Ariens and Simonis (1964, Molecular Pharmacology, Vol. 1, New York, Academic Press, 119) and mean values are plotted. Horizontal error bars represent SEM of pEC$_{50}$ values.

To the extent that inotropic effects of serotonin have been demonstrated in the rat heart, these have been confined to the atrium and have been mediated by 5-HT$_{2A}$-receptors (Laer et al., 1998, supra). To test whether 5-HT$_2$-receptors could also be involved in the inotropic effect of serotonin in papillary muscle from Chronic heart failure rats, we used the 5-HT$_{2A}$ receptor antagonist ketanserin. Ketanserin (0.1 µmol/l) did not shift the concentration-response curve for serotonin to higher concentrations of agonist (pD$_2$-value with ketanserin 7.49±0.08 (SEM, n=5) vs. 7.62±0.06 (SEM, n=6) without, p=0.24, unpaired Students t-test), suggesting that the 5-HT$_{2A}$-receptor is not involved in the inotropic response to serotonin in papillary muscles from post-MI Chronic heart failure rats (FIG. 5). There was no significant difference between the maximal inotropic responses in the two groups (with and without ketanserin), measured at the top of each concentration-response curve (pooled result 17.5±1.9% (SEM, n=11)). The apparently lower inotropic effect in this experiment compared to that in e.g. FIG. 2a illustrates a consistently lower inotropic effect in all experiments when measured after a full concentration-response curve as opposed to a direct stimulation with a high concentration (e.g., 10 µmol/l) of serotonin. This difference may reflect desensitisation of the response during the continuous stimulation with increasing concentrations of serotonin, as is done to achieve the concentration-response curves.

High Affinity of GR113808 Documents Involvement of 5-HT$_4$ Receptors

Figure 6:
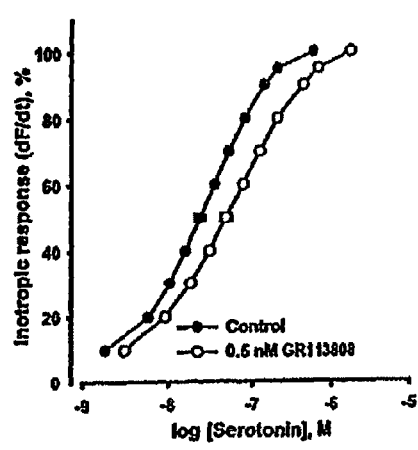
FIG. 6 shows that the high affinity of GR 113808 confirms involvement of 5-HT$_4$-receptors. Concentration-response curves for serotonin in papillary muscles from Chronic heart failure rats in the absence and presence of 0.5 nmol/l GR 113808. The experiments were performed in the presence of 0.1 µmol/l ketanserin and data were analysed and expressed as in FIG. 5.

To provide pharmacological evidence for the involvement of 5-HT$_4$ receptors, the shift of the concentration-response curve to serotonin by GR113808 was determined. The experiment was performed in the presence of 0.1 µmol/l ketanserin to block 5-HT$_{2A}$ receptors, if present. The concentration-response curves to serotonin in the absence and presence of 0.5 nmol/l GR113808 were essentially parallel with pEC$_{50}$-values of 7.62±0.06 (SEM, n=6) and 7.32±0.06 (SEM, n=6, p<0.005), respectively (FIG. 6), with no difference in the maximum inotropic response induced by serotonin between the groups (pooled average 18.7±2.4% (SEM, n=12)). The corresponding GR113808 inhibition constant (K$_b$) calculated from the Schild equation was 0.5 nmol/l, corresponding to a pK$_b$ value of 9.3. Since GR113808 displays at least 1000-fold selectivity for the 5-HT$_4$ receptor over all other known receptors, this provides strong evidence for a 5-HT$_4$ receptor-mediated inotropic response to serotonin in papillary muscle from Chronic heart failure rats.

TABLE 1

Qualitative characteristics of the contraction-relaxation cycles (CRC) in Chronic heart failure and sham-operated animals before and after subsequent addition of serotonin (10 µmol/l) and isoprenaline (100 µmol/l), respectively.

|  | Control (ms) | 5-HT (ms) | 5-HT (% of control) | ISO (ms) | Iso (% of control) |
|---|---|---|---|---|---|
|  |  | Sham N = 6 |  |  |  |
| TPF | 125.1 ± 5.5 | 123.7 ± 5.5 | 99.0 ± 0.8 | 109.3 ± 2.7 | 87.4 ± 2.3 |
| TR20 | 233.6 ± 11.2 | 231.0 ± 11.0 | 99.0 ± 0.7 | 174.0 ± 4.9 | 74.5 ± 1.7 |
| RT (TR20−TPF) | 108.4 ± 6.2 | 107.3 ± 5.9 | 99.0 ± 0.5 | 75.0 ± 2.5 | 69.4 ± 3.2 |
|  |  | CHF n = 10 |  |  |  |
| TPF | 148 ± 3.9 | 134 ± 3.5 | 90.5 ± 1.4 | 123.1 ± 1.6 | 83.2 ± 1.7 |
| TR20 | 254.3 ± 6.3 | 224.6 ± 5.4 | 88.3 ± 1.5 | 204.1 ± 2.9 | 80.3 ± 1.9 |
| RT (TR20−TPF) | 106.3 ± 2.5 | 90.6 ± 2.2 | 85.2 ± 1.5 | 81.0 ± 1.8 | 76.2 ± 1.8 |

Values are mean ± SEM of average results from 20-40 CRC in each group of papillary muscles.
TPF = Time to peak force
TR2O = Time to relaxation to 20% level
RT = Relaxation time

EXAMPLE 2

Quantitative Reverse Transcriptase Polymerase Chain Reaction (RT-PCR) to Examine 5-HT4 Receptor mRNA Induction in CHF Non-infarcted left ventricle tissue (30-50 mg, mainly septum), collected immediately after removal of the papillary muscle, or papillary muscle (15-30 mg including some left ventricular wall) collected after completion of functional analyses, stored in RNAlater (Ambion) until use, was flash frozen and reduced to powder under liquid nitrogen. Total RNA was isolated from tissue powder homogenized in 1 ml TRIZOL (Invitrogen), followed by mRNA extraction (Bach et al. 2001 supra) and oligo-dT-primed first strand cDNA synthesis (Medhurst et al. 2001 Brain Res Mol Brain Res 90: 125-134). A standard curve with 5-300 ng mRNA was made to control for reverse transcription and PCR quantification.

Sets of primers (targeted to intron/exon boundaries to avoid genomic DNA signals) and probes (Double-Dye Oligonucleotide, Eurogentec, 5'-labeled with the fluorescent reporter dyes FAM (5-HT$_{4(b)}$, GI:924649 (Gerald et al. 1995 EMBO J. 14: 2806-2815) and 5-HT$_{2A}$, GI:207067 (Julius et al. 1990 PNAS USA 87: 928-932)), JOE (Eurogentec; glyceraldehyde-3-phosphate dehydrogenase (GAPDH; GI:10190788)) or Yakima Yellow (YY; Eurogentec; atrial natriuretic peptide (ANP; GI:55711)) and quenched with TAMRA (5-HT$_{4(b)}$, 5-HT$_{2A}$ and GAPDH) or Dark Quencher (DQ; Eurogentec; ANP)) for quantitative PCR were designed as described (Bustin et al. 2000 J. Mol. Endocrinol 25: 169-193). The names and sequences of upper (U) and lower (L) primers and probes (P) used were (5'-3'): 5-HT$_{4(b)}$: ON283 (U), CATGTGCATAGGTATACAGTGGAATGT (SEQ ID NO: 1); ON284 (L), GCAGCCACCAAAGGAGAAGTT (SEQ ID NO: 2); TM14(P), FAM-CCATCTGCTGCCAGC-CTTTGGTCTATAGGA-TAMRA (SEQ ID NO: 3); 5-HT$_{2A}$: ON273(U); TTCACCACAGCCGCTTCAA (SEQ ID NO: 4); ON274(L), ATCCTGTAGTCCAAAGACTGGGATT (SEQ ID NO: 5); TM9(P), FAM-ATGGATATACCTACA-GATATGGTCGTCCACACGGCAAT-TAMRA (SEQ ID NO: 6); ANP: ON285(U), ATCTGATGGATTTCAA-GAACC (SEQ ID NO: 7); ON286(L), CTCTGAGACGGGT-TGACTTC (SEQ ID NO: 8); TM15(P) YY-CGCTTCATCG-GTCTGCTCGCTCA-DQ (SEQ ID NO: 9); GAPDH: ON279(U), CCTGCACCACCAACTGCTTA (SEQ ID NO: 10); ON290(L), GGCATGGACTGTGGTCATGA (SEQ ID NO: 11); TM12(P), JOE-TGGCCAAGGTCATCCATGA-CAACTTTG-TAMRA (SEQ ID NO: 12).

Quantitative RT-PCR (Medhurst et al. supra) was done in 25 µl reactions with TaqMan Universal PCR Master Mix (Applied Biosystems) containing 5 mM Mg$^{2+}$, 300 nM of each primer, 200 nM probe and long template cDNA. GAPDH was quantified separately for normalization with 0.1 ng cDNA template. Raw data were collected and analyzed with Sequence Detector Software (SDS version 1.7; Applied Biosystems) (Bustin et al. 2000, supra). Results are expressed as mean±SEM from n animals. P<0.05 was considered statistically significant (nonparametric Mann-Whitney test).

Induction of 5-HT4(b) Receptor mRNA in CHF

Figure 7:
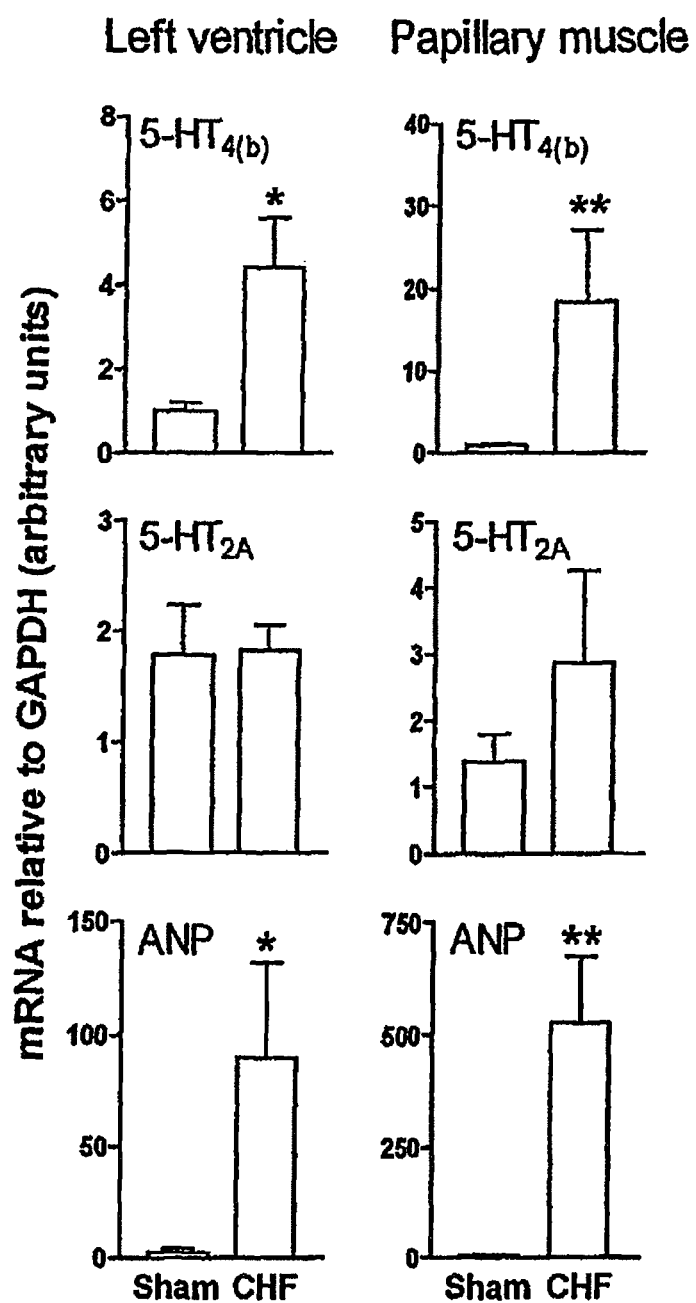
FIG. 7 shows expression of 5-HT$_{4(b)}$, 5-HT$_{2A}$ and ANP mRNA in left ventricle and papillary muscle of sham treated and CHF rats. Messenger RNA for 5-HT$_{4(b)}$ receptor (upper panels), 5-HT$_{2A}$ receptor (middle panels) and ANP (lower panels) was quantified, and normalised to GAPDH. *CHF vs Sham p<0.01, **CHF vs Sham P<0.05.

Quantitative RT-PCR was used to determine the level of mRNA encoding 5-HT$_{4(b)}$ receptor, 5-HT$_{2A}$ receptor, and the heart failure marker ANP normalized to the level of GAPDH mRNA. In left ventricle and papillary muscle, respectively, 5-HT$_{4(b)}$ mRNA levels were four and 18-fold higher in CHF vs. Sham, whereas 5-HT$_{2A}$ mRNA levels were unchanged and ANP mRNA levels increased (FIG. 7). The ratio between normalized 5-HT$_{4(b)}$ and 5-HT$_{2A}$ mRNA levels was increased in CHF in both left ventricle and papillary muscle, confirming increased 5-HT$_{4(b)}$ mRNA level relative to 5-HT$_{2A}$, independent of GAPDH (Table 2).

EXAMPLE 3

Figure 8:
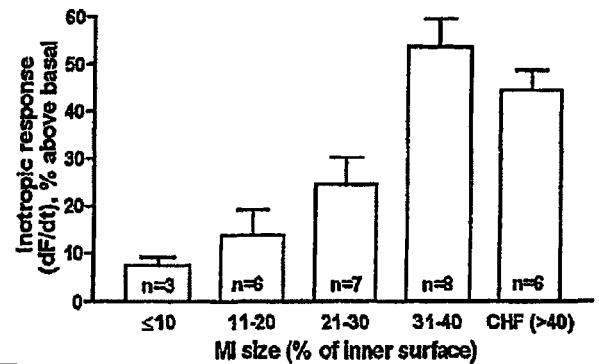
FIG. 8 shows the relationship between the maximum inotropic response to 10 µM serotonin in papillary muscle and infarction size (A) and 5-HT$_4$, 5-HT$_{2A}$ and ANP mRNA levels in non-infarcted left ventricle tissue related to infarction size (B).
Figure 8:
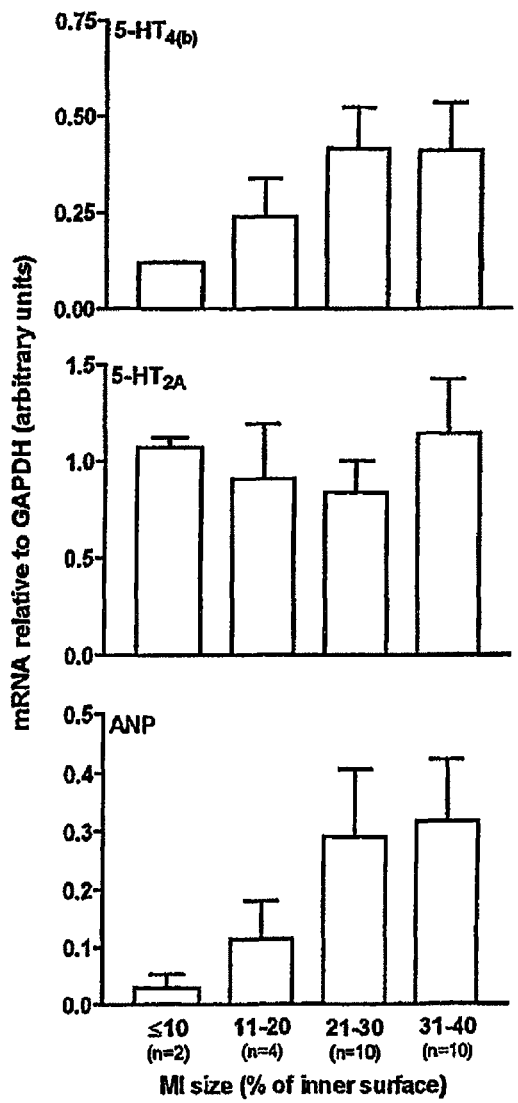
Figure 9:
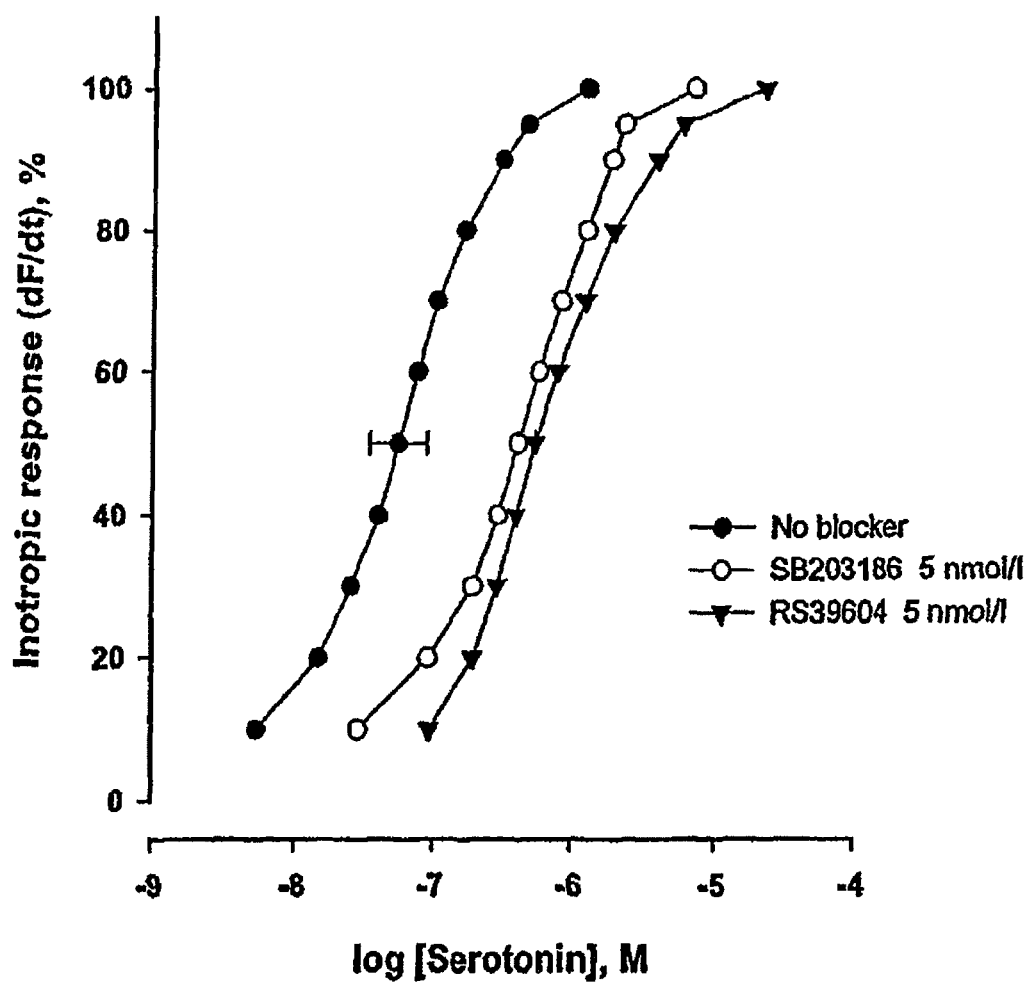
FIG. 9 shows concentration-response curves for serotonin in papillary muscles of rats 6 weeks after myocardial infarction in the absence and presence of 5 nM SB203186 or 5 nm RS39604. Inotropic response (dF/dt) is expressed in percent of maximum for each papillary muscle.

The Maximum Inotropic Response to Serotonin and 5-HT$_{4(b)}$ Receptor mRNA Related to Infarction Size In papillary muscles from MI$_{nf}$ rats i.e., rats in which symptoms of CHF were not obtained, despite having undergone surgery to induce myocardial infarction, serotonin (10 µM) elicited an inotropic response qualitatively similar to the response observed in CHF animals. The magnitude of the response correlated positively with infarction size up to 30-40% of the inner myocardial surface in MI$_{nf}$ animals (FIG. 8A). In MI$_{nf}$ hearts with infarct size 30-40% the inotropic effect was of the same magnitude as in CHF hearts which all had infarct size >40%. A positive correlation with infarction size was also observed for 5-HT$_{4(b)}$ and ANP mRNA expression, whereas 5-HT$_{2A}$ mRNA levels were unchanged (FIG. 8B). These findings suggest a gradual transition related to the extent of myocardial changes secondary to the infarction.

TABLE 2

Ratio of 5-HT$_{4(b)}$ receptor mRNA to 5-HT$_{2A}$ receptor mRNA

|  | Sham | CHF |
|---|---|---|
| Left ventricle | 0.87 ± 0.33 (n = 7) | 3.20 ± 1.09 (n = 11)* |
| Papillary muscle | 0.85 ± 0.64 (n = 4) | 7.48 ± 2.44 (n = 5)† |

To test the observation of increased 5-HT$_{4(b)}$ receptor level independent of GAPDH the ratio of normalized 5-HT$_{4(b)}$ receptor mRNA to normalized 5-HT$_{2A}$ receptor mRNA was calculated. *CHF vs. Sham p<0.06; †CHF vs. Sham p<0.05.

EXAMPLE 4

The inotropic response to serotonin in papillary muscle from 6 week post myocardial infarction rats was measured in the presence of several chemically different 5-HT$_4$ receptor antagonists, as described above.

The 5-HT$_4$ antagonists SB203186 and RS39604, each added at 5 mM, block the inotropic response to serotonin in 6 week post MI rats with blocking potencies corresponding to their known affinities at 5-HT$_4$ receptors. The figure shows concentration-response curves for serotonin in papillary muscles of rats 6 weeks after myocardial infarction in the absence and presence of 5 nM SB203186 or 5 nM RS39604. Inotropic response (dF/dt) is expressed in percent of maximum for each papillary muscle.

The pEC$_{50}$ value for serotonin in the absence of blocker was 7.25±0.2. The pEC$_{50}$ value for serotonin in the presence of 5 nM SB203186 was 6.39, corresponding to a pK$_b$ value of 9.1. The pEC$_{50}$ value for serotonin in the presence of 5 nM RS39604 was 6.26, corresponding to a pK$_b$ value of 9.2. This is consistent with the inotropic response to serotonin being mediated via 5-HT$_4$ receptors.

EXAMPLE 5

5-HT$_4$ Receptor-Mediated Inotropic Responses in Rat Hypertensive Heart Failure A second model of heart failure was then used to study the 5-HT$_4$ receptor-mediated inotropic effect of serotonin; namely a model of rat hypertensive heart failure. This study uses a rat model of heart failure obtained by aortic banding. In this model, the heart failure is induced by a constantly increased afterload, somewhat reminiscent of human hypertensive heart failure. This study was performed to clarify whether it is the heart failure as such, or the cardiac infarction preceding the heart failure that underlies the induction of 5-HT$_4$ receptors in the post-infarction model.

Trans-aortic constriction (aortic banding) of the ascending aorta was induced in 200 g male Wistar rats under anaesthesia, induced by 63% N$_2$O, 32% O$_2$ and 5% Isoflurane and maintained by 66% N$_2$O, 33% O$_2$ and 1-2% Isoflurane. A right-sided thoracotomi was performed through a 3-4 cm long cutaneous incision, the pericardium was opened and the ascending aorta identified and dissected free of surrounding tissue. A ligature was knit around the ascending aorta and a metal probe with diameter 0.9 mm. The metal probe was then removed. The result was a constriction of the ascending aorta with internal diameter about 0.9 mm. The thorax was then closed with 3-0 silk sutures and the skin closed with Dexon 1 sutures. The animals received post-operative analgesia with buprenorphine 0.09 mg subcutaneously and were allowed to wake up in a 30° C. environment. After six weeks the animals were again placed under anaesthesia as during the primary surgery, and an echocardiographic examination was performed. Finally the thorax was opened and the heart was removed for preparation of posterior left ventricular papillary muscles as described (Sjaastad et al. 2003 Acta physiol Scand 177: 449-458). The rat was considered to have CHF.

Papillary muscle was extracted from a CHF rat 6 weeks after aortic banding as described above. osterior left ventricular papillary muscle was prepared, mounted in organ bath, equilibrated and field stimulated at 1 Hz (Sjaastad et al. 2003 supra), and the contraction-relaxation cycles (CRCs) were recorded and analysed as previously described (Skomedal et al. 1997, J. Pharmacol Exp Ther 280: 721-729) (Sjaastad et al., 2003, supra) with respect to maximal developed force (F$_{max}$), maximal development of force (dF/dt)$_{max}$, time to peak force (TPF), time to relaxation to 20% level (TR20) and relaxation time (RT=TR20-TPF). The experiment was performed in the presence of blockers (added 90 min prior to serotonin) of adrenergic and muscarinic cholinergic receptors (prazosin 1 µM, timolol 1 µM, atropine 1 µM).

Figure 10:
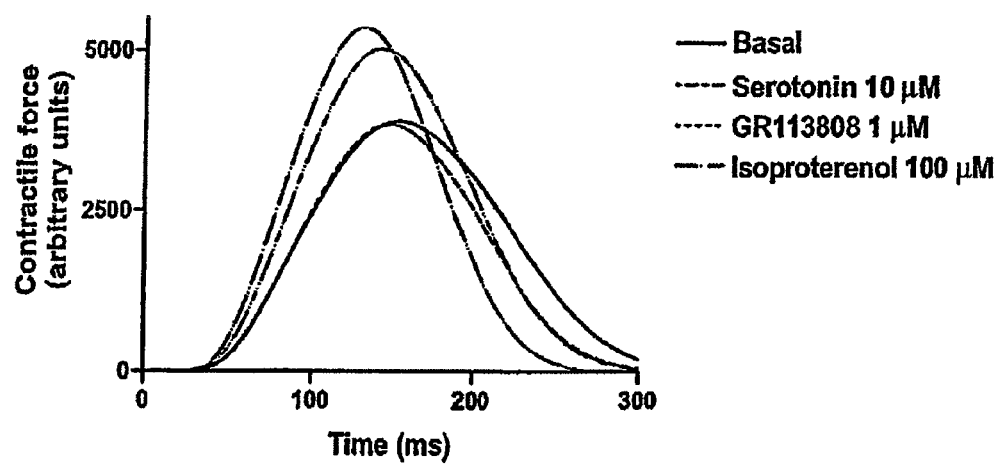
FIG. 10 shows representative average contraction-relaxation cycles in a papillary muscle from the heart of a rat with CHF 6 weeks after aortic banding before addition of agonist, at maximal steady state inotropic response to 10 µM serotonin, following reversal of the serotonin response with 1 µM GR113808 and at maximal steady state inotropic response to 100 µM isoproterenol.

FIG. 10 shows representative average contraction-relaxation cycles in a papillary muscle from the heart of a rat with CHF 6 weeks after aortic banding before addition of agonist, at maximal steady state inotropic response to 10 µM serotonin, following reversal of the serotonin response with 1 µM GR113808 and at maximal steady state inotropic response to 100 µM isoproterenol. Serotonin (10 µM) elicited a positive inotropic response comparable in magnitude and characteristics to the positive inotropic response to 100 µM isoproterenol (enough to surmount the blockade by 1 µM timolol). The positive inotropic response to serotonin was reversed by 1 µM of the 5-HT$_4$ antagonist GR113808, indicating that the response is mediated through 5-HT$_4$ receptors.

This shows that this model of heart failure in rats also causes the appearance of a 5-HT$_4$ receptor-mediated inotropic response to serotonin, indicating that this finding is general for heart failure as such, at least in rats.

EXAMPLE 6

5-HT$_4$ Receptor-Mediated Inotropic Effect of Serotonin in Human Heart

To study the 5-HT$_4$ receptor-mediated inotropic response to serotonin in human heart, trabecular muscle from a post-infarct human heart and a human heart with heart failure due to dilated cardiomyopathy was used.

Figure 11:
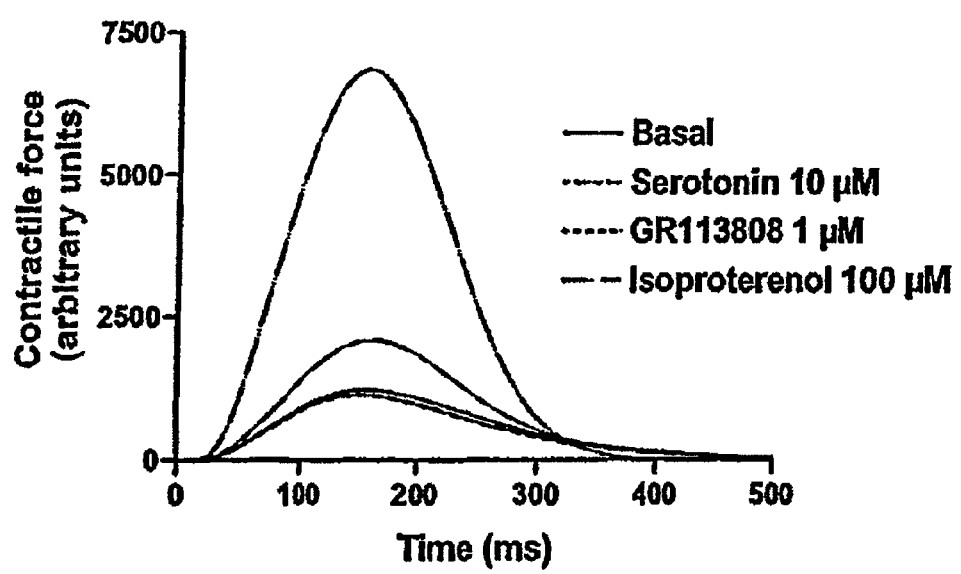
FIG. 11 shows representative average contraction-relaxation cycles in a trabecular muscle from an explanted human heart before addition of agonist, at maximal steady state inotropic response to 10 µM serotonin, following reversal of the serotonin response with 1 µM GR 13808 and at maximal steady state inotropic response to 100 µM isoproterenol.

FIG. 11 shows representative average contraction-relaxation cycles in a trabecular muscle from the explanted post infarct human heart before addition of agonist, at maximal steady state inotropic response to 10 µM serotonin, following reversal of the serotonin response with 1 µM GR 13808 and at maximal steady state inotropic response to 100 µM isoproterenol.

The heart was explanted from a patient who had survived a small myocardial infarction and died in hospital from subarachnoidal haemorrhage. Trabecular muscles were prepared, mounted in organ baths, equilibrated and field stimulated at 1 Hz (Skomedal et al., 1997, supra) and the contraction-relaxation cycles (CRCs) were recorded and analysed as previously described (Skomedal et al., 1997, supra) with respect to maximal developed force ($F_{max}$), maximal development of force $(dF/dt)_{max}$, time to peak force (TPF), time to relaxation to 20% level (TR20) and relaxation time (RT=TR20-TPF). The experiment was performed in the presence of blockers (added 90 min prior to serotonin) of adrenergic and muscarinic cholinergic receptors (prazosin 1 µM, timolol 1 µM, atropine 1 µM).

As seen in FIG. 11, serotonin (10 µM) elicited a positive inotropic response amounting to about 10% of the positive inotropic response to 100 µM isoproterenol (enough to surmount the blockade by 1 µM timolol). The positive inotropic response to serotonin was reversed by 1 µM of the 5-$HT_4$ receptor antagonist GR113808, indicating that the response is mediated through 5-$HT_4$ receptors.

A heart was also explanted from a patient who had received a heart transplant due to heart failure from dilated cardiomyopathy. Trabecular muscles were prepared and the contraction-relaxation cycles (CRCs) were recorded and analysed as described above. In addition to the presence of blockers as above, the positive inotropic responses to serotonin and isoproterenol were enhanced by the presence of the phosphodiesterase inhibitor IBMX (isobutyl-methyl-xanthine; 35 µM).

Figure 12:
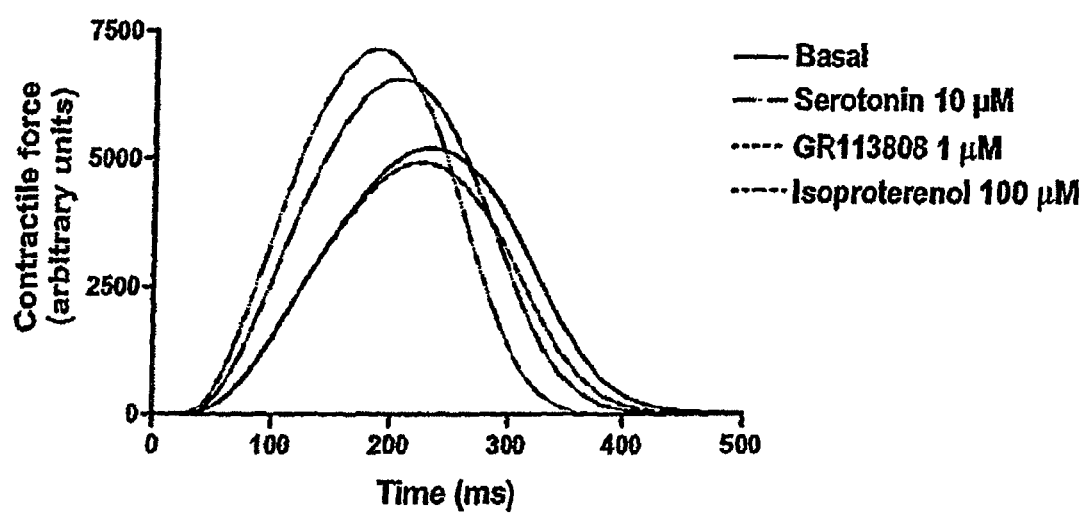
FIG. 12 shows representative average contraction-relaxation cycles in a trabecular muscle from an explanted human heart before addition of agonist, at maximal steady state inotropic response to 10 µM serotonin, following reversal of the serotonin response with 1 µM GR113808 and at maximal steady state inotropic response to 100 µM isoproterenol.

FIG. 12 shows representative average contraction-relaxation cycles in a trabecular muscle from this explanted human heart before addition of agonist, at maximal steady state inotropic response to 10 µM serotonin, following reversal of the serotonin response with 1 µM GR113808 and at maximal steady state inotropic response to 100 µM isoproterenol.

As seen in the figure, serotonin (10 µM) elicited a positive inotropic response amounting to about 32% of the positive inotropic response to 100 µM isoproterenol (enough to surmount the blockade by 1 µM timolol). The positive inotropic response to serotonin was reversed by 1 µM of the 5-$HT_4$ receptor antagonist GR113808, indicating that the response is mediated through 5-$HT_4$ receptors.

This shows that the presence of an inotropic response through 5-$HT_4$ receptors in the failing heart is also seen in humans.

EXAMPLE 7

Effect of Treatment of Post-Infarction Congestive Heart Failure (CHF) Rats with a 5-$HT_4$ Antagonist An extensive myocardial infarction (MI) was induced in 320 g male Wistar rats under anaesthesia (68% $N_2O$, 29% $O_2$ and 2-3% Isofluran) by a proximal ligation of the left coronary artery (Sjaastad et al. 2003, supra). Three days later, rats were included in the study if the rats had both clinical signs of congestive heart failure (tachypnoe and forced ventilation) and a large myocardial infarction as verified by echocardiography. Rats included in the study were randomized blindly to placebo or treatment.

Under anesthesia with 75 µg/kg Fentanyl (Janssen Pharmaceutical) and 3.75 mg/kg Midazolam (Roche) s.c., as well as local anesthesia with Xylocaln 1% around the incision, the rats received subcutaneous implantation of 2 ml Alzet miniosmotic pumps (Alza, Palo Alto, Calif.) containing solvent (100 µM ascorbic acid, 50 µM EDTA in water; placebo group) or solvent containing 50 mM of the 5-$HT_4$ antagonist SB207266 (treatment group). The pumps were replaced with new pumps after three weeks to obtain a total treatment time of six weeks.

After six weeks of treatment, the animals were again placed under Isofluran anaesthesia (68% $N_2O$, 29% $O_2$ and 2-3% Isofluran) with temperature control for echocardiographic and hemodynamic measurements, followed by euthanasia. Posterior left ventricular papillary muscles were then prepared, mounted in organ baths, equilibrated and field stimulated at 1 Hz (Sjaastad et al., 2003 supra) and the contraction-relaxation cycles (CRCs) were recorded and analysed as previously described with respect to maximal developed force ($F_{max}$), maximal development of force $(dF/dt)_{max}$, time to peak force (TPF), time to relaxation to 20% level (TR20) and relaxation time (RT=TR20-TPF).

The experiments were performed in the presence of blockers (added 90 min prior to agonist) of α-adrenergic and muscarinic cholinergic receptors (prazosin 1 µM, atropine 1 µM). Isoproterenol was added to the organ bath cumulatively and the maximal positive inotropic response to isoproterenol was calculated for each animal.

Figure 13:
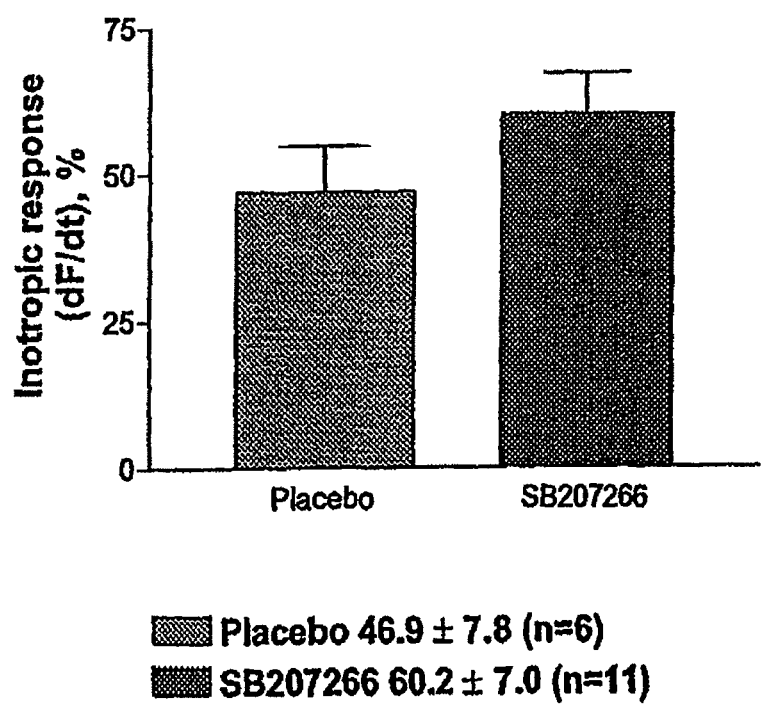
FIG. 13 shows maximal inotropic response to β adrenoceptor stimulation in rats with CHF treated for six weeks with SB207266 or placebo.

The results are shown in FIG. 13 and indicate a trend towards normalisation of myocardial function, as judged by the trend towards normalisation of the CHF-induced reduction of maximal inotropic response to β-adrenoceptor stimulation, by treatment with the 5-$HT_4$ antagonist SB207266.

Furthermore, in CHF, the duration of the contraction-relaxation cycle is prolonged, due to changes in myofilament composition. Therefore, the duration of the contraction-relaxation cycle can be used as an additional parameter of the degree of myocardial dysfunction. Our preliminary data from treatment with the 5-$HT_4$ antagonist SB207266 also show a trend towards normalisation of this parameter of myocardial dysfunction (data not shown).

EXAMPLE 8

| Tablets (Oral) for Treatment and Prophylaxis of Heart Failure | |
|---|---|
| GR113808 (as hydrochloride salt) | 10.95 g |
| lactose | 157 g |
| microcrystalline cellulose | 30 g |
| magnesium stearate BP | 2.05 g |

The active ingredients are passed through a 24 mesh sieve and blended with lactose, microcrystalline cellulose and magnesium stearate. The resulting mixture is pressed into tablets. Tablet weight is 200 mg and each tablet contains 10 mg GR 13808.

EXAMPLE 9

| Capsules (Oral) for Treatment and Prophylaxis of Heart Failure | |
|---|---|
| SB207266 (as hydrochloride salt) | 5.5 g |
| Atenolol | 25 g |
| lactose | 169.5 g |

The active ingredients are passed through a 24 mesh sieve and blended with lactose. The mixture is filled into gelatin capsules (200 mg) using suitable machinery. Each capsule contains 5 mg SB207266 and 50 mg atenolol.

EXAMPLE 10

| Solution for Injection for Treatment and Prophylaxis of Heart Failure | |
|---|---|
| SB207266 (as hydrochloride salt) | 10.9 g |
| sodium chloride | q.s. |
| water for injection | ad. 10 litre |

SB207266 (as hydrochloride salt) and sodium chloride are dissolved in water for injection to form an isotonic solution. The mixture is filled into vials (10 ml) with rubber stoppers and sterilised by heating in an autoclave for 20 minutes at 121 degrees centrigrade. Each vial contains 10 ml and 1 mg SB207266 per ml.

EXAMPLE 11

| Capsules (Oral) for Treatment and Prophylaxis of Heart Failure | |
| --- | --- |
| SB207266 (as hydrochloride salt) | 5.5 g |
| metoprolol tartrate | 50 g |
| lactose | 144.5 g |

The active ingredients are passed through a 24 mesh sieve and blended with lactose. The mixture is filled into gelatin capsules (200 mg) using suitable machinery. Each capsule contains 5 mg SB207266 and 50 mg metoprolol tartrate.

EXAMPLE 12

| Capsules (Oral) for Treatment and Prophylaxis of Heart Failure | |
| --- | --- |
| SB207266 (as hydrochloride salt) | 5.5 g |
| enalapril maleate | 10 g |
| lactose | 184.5 g |

The active ingredients are passed through a 24 mesh sieve and blended with lactose. The mixture is filled into gelatin capsules (200 mg) using suitable machinery. Each capsule contains 5 mg SB207266 and 10 mg enalapril maleate.

EXAMPLE 13

| Capsules (Oral) for Treatment and Prophylaxis of Heart Failure | |
| --- | --- |
| SB207266 (as hydrochloride salt) | 5.5 g |
| losartan potassium | 50 g |
| lactose | 169.5 g |

The active ingredients are passed through a 24 mesh sieve and blended with lactose. The mixture are filled into gelatin capsules (200 mg) using suitable machinery. Each capsule contains 5 mg SB207266 and 50 mg losartan potassium salt.

EXAMPLE 14

| Capsules (Oral) for Treatment and Prophylaxis of Heart Failure (5HT$_4$ Receptor Antagonist Plus α/β-Blocker) | |
| --- | --- |
| SB207266 (as hydrochloride salt) | 5.5 g |
| carvedilol | 12.5 g |
| lactose | 182 g |

The active ingredients are passed through a 24 mesh sieve and blended with lactose. The mixture is filled into gelatin capsules (200 mg) using suitable machinery. Each capsule contains 5 mg SB207266 and 12.5 mg carvedilol.

EXAMPLE 15

| Suppositories for Treatment and Prophylaxis of Heart Failure | |
| --- | --- |
| GR113808 (as hydrochloride salt) | 16.5 g |
| Glyceride mixture of fatty acid | 193.5 g |

GR113808 salt is milled down to a particle size of approximately 20 microns. A suspension of the salt is prepared in molten glyceride of fatty acid and filled into suppository moulds. The weight of each suppository is 200 mg with unit dose of 15 mg GR113808.

What is claimed is:

1. A method for treating heart failure characterized by impaired ventricular function in a mammal, said method comprising:
   identifying a mammal that suffers from heart failure characterized by impaired ventricular function, wherein said mammal does not have atrial arrhythmia, and
   administering to said mammal a pharmaceutically effective amount of a 5-$HT_4$ receptor antagonist or a pharmaceutically acceptable salt thereof to inhibit activity or activation of 5-$HT_4$ receptors in the ventricles, thereby inhibiting an inotropic response in the ventricles mediated by said receptors.

2. The method of claim 1, wherein said heart failure is characterized by a left ventricular ejection fraction (LVEF) of less than 40%.

3. The method of claim 1 wherein said heart failure is chronic heart failure, congestive heart failure, or post-infarction heart failure.

4. The method of claim 3 wherein said congestive heart failure is chronic congestive heart failure.

5. The method of claim 1 wherein said heart failure results from ischaemic heart disease or chronic non-ischaemic cardiomyopathy.

6. The method of claim 5 wherein
   (i) said ischaemic heart disease is chronic ischaemic heart disease; or
   (ii) said chronic non-ischaemic cardiomyopathy is idiopathic dilated cardiomyopathy (IDCM) or cardiomyopathy due to hypertension.

7. The method of claim 1 wherein said heart failure is of class II, III or IV of the NYHA classification system.

8. The method of claim 1, wherein said 5-$HT_4$ receptor antagonist is selected from compounds comprising an aromatic ring structure with a hydrogen-bond acceptor as one substituent and a hydrogen-bond acceptor as a second substituent and a tertiary amine spaced at least three bonds away from the aromatic ring.

9. The method of claim 1, wherein said 5-$HT_4$ receptor antagonist comprises an aromatic ring to which a carbonyl group is attached, and a basic nitrogen in an appended side chain and an oxygen atom adjacent to the carbonyl group.

10. The method of claim 1, wherein said 5-$HT_4$ receptor antagonist is selected from the group consisting of benzoate esters, benzoate amides, imidazolopyridines, aryl ketones, indoles, carbazimidamides, phenylcarbamates and phenylureas.

11. The method of claim 1, wherein said 5-$HT_4$ receptor antagonist is selected from the group consisting of 1-piperidinyl-ethyl-1H-indole-3-carboxylate, SB203186; (1 butyl 4 piperidinyl)methyl 8 amino 7 iodo-1,4 benzodioxan 5 carboxylate, SB207710; [1[2 methylsulphonylamino ethyl]-4-piperidinyl]-methyl 1H indole 3 carboxylate, GR113808; 2 diethylaminoethyl (2 methoxy 4 amino 5 chloro)benzoate, SDZ205557; endo 8 methyl 8 azabicyclo[3.2.1]

oct 3 yl 2,3 dihydro 6 methoxy 2 oxo 1H benzimidazole 1 carboxylate, DAU 6285; 1[4 amino 5 chloro 2 (3,5 dimethoxybenzyl-oxy)phenyl]3[1[2[(methylsulfonyl) amino]ethyl]4 piperidinyl]1 propanone hydrochloride, RS 39604; (1 n butyl 4 piperidinyl)methyl 8 amino 7 chloro 1, 4 benzodioxane 5 carboxylate, SB 204070; N[(1 butyl 4 piperidinyl)-methyl]3,4dihydro 2H[1,3]oxazino[3,2 a]indole10-carboxamide hydrochloride, SB 207266; (endo 3,9 dimethyl 3,9 diazabicyclo[3,3,1]non 7 yl 1H indazole 3 carboxamide dihydrochloride), N 3389; [(+) 8,9 dihydro 10 methyl 7[(5 methyl 4 imidazolyl)methyl]pyrido[1,2 a]indole 6(7H) one hydrochloride], FK1052; 2 (cis 3,5 dimethyl-piperidino)ethyl 4 amino 5 chloro 2 methoxybenzoate, ML10375; [3 (piperidine 1 yl)propyl 4 amino 5 chloro 2 methoxybenzoate hydrochloride], RS 23597 190; (1-[2-[(methyl-sulphonyl)amino]-ethyl]-4-piperidinyl-methyl-5-fluoro-2-methoxy-1H-indole-3-carboxylate), GR125487; R50595 (FR76530); RS100302; 1-(1-methylethyl)-N-[2-[4-[tricyclo[3.3.1.1(3,7)]dec-1-ylcarbonyl)amino]-1-piperidinyl]ethyl-1H-indazole-3-carboxamide, LY353433; A-85380; SB205800; SB 207058; SC-53606 and SC 56184.

12. The method of claim 1, wherein said 5-$HT_4$ receptor antagonist is an antibody or fragment or derivative thereof.

13. The method of claim 1, wherein said 5-$HT_4$ receptor antagonist is formulated as a physiologically acceptable salt.

14. The method of claim 1, wherein the 5-$HT_4$ receptor antagonist blocks a response to 5-HT.

15. The method of claim 1, wherein the 5-$HT_4$ receptor antagonist is formulated for oral administration or parenteral administration.

16. The method of claim 1 wherein cardiac performance is improved following administration of the 5-$HT_4$ receptor antagonist.

17. The method of claim 16, wherein the improvement is:
(i) ventricular ejection fraction is increased; or
    (ii) one or more of the following: New York Heart Association (NYHA) functional class is reduced, exercise capacity is improved and haemodynamic status and echocardiographic variables are improved; or
    (iii) the plasma level of Nt-proANP is reduced.

18. The method of claim 17, wherein
(i) left ventricular ejection fraction is increased; or
    (ii) the improved haemodynamic status and echocardiographic variables are one or more of the following: pulmonary capillary wedge pressure is decreased, pulmonary artery pressure is decreased, peak heart rate is increased, peak systolic blood pressure is increased and mitral velocity deceleration time is increased.

19. The method of claim 1, further comprising assessing said mammal for:

(i) an improvement in said heart failure following administration of said antagonist; or
(ii) an improvement in cardiac function or an improvement of a symptom or parameter of the heart failure following administration of said antagonist.

20. The method of claim 19, wherein said assessing comprises one or more selected from the group consisting of:
    (i) assessing the NYHA functional class of said mammal;
    (ii) assessing one or more haemodynamic status indicators or echocardiographic variables selected from exercise capacity, pulmonary capillary wedge pressure, pulmonary artery pressure, peak heart rate, peak systolic blood pressure, or mitral velocity deceleration time;
    (iii) measuring ventricular ejection fraction;
    (iv) measuring left ventricular ejection fraction;
    (v) measuring plasma levels of Nt-proANP;
    (vi) assessing response to 5HT; and
    (vii) assessing coronary artery disease, primary or secondary cardiomyopathy, hypertension, valvular disease, or congenital heart defects in said mammal.

21. The method of claim 1, further comprising administering to said mammal a second agent in an amount that is effective to treat heart failure.

22. The method of claim 21, wherein said second agent is administered simultaneously or sequentially with respect to the 5-$HT_4$ receptor antagonist.

23. The method of claim 21, wherein said second agent is selected from the group consisting of diuretics, vasodilators, inotropic drugs, anticoagulants, β blockers, angiotensin II blockers, angiotensin converting enzyme inhibitors, and aldosterone antagonists.

24. The method of claim 21 wherein said second agent is a β blocker.

25. A method for treating heart failure characterized by impaired ventricular function in a mammal, wherein said mammal does not have atrial arrhythmia, said method comprising:
    administering to a mammal that suffers from heart failure characterized by impaired ventricular function and that does not have atrial arrhythmia a pharmaceutically effective amount of a 5-$HT_4$ receptor antagonist or a pharmaceutically acceptable salt thereof to inhibit activity or activation of 5-$HT_4$ receptors in the ventricles, thereby inhibiting an inotropic response in the ventricles mediated by said receptors, and
    assessing said mammal for an improvement in said heart failure characterized by impaired ventricular function following administration of said antagonist.

* * * * *